(12) United States Patent
Doutt et al.

(10) Patent No.: US 10,895,565 B2
(45) Date of Patent: Jan. 19, 2021

(54) ANALYSIS SYSTEM AND METHOD FOR DETECTING VOLATILE ORGANIC COMPOUNDS IN LIQUID

(71) Applicant: Parker-Hannifin Corporation, Cleveland, OH (US)

(72) Inventors: Michael Lewis Doutt, Madison, AL (US); Glenn Stacey Geis, Huntsville, AL (US); Kazi Z. A. Hassan, Huntsville, AL (US); Walter C. Cameron, Clanton, AL (US); Taylor J. Wingo, Birmingham, AL (US); Gottfried P. Kibelka, Hoover, AL (US)

(73) Assignee: Parker-Hannifin Corporation, Cleveland, OH (US)

( * ) Notice: Subject to any disclaimer, the term of this patent is extended or adjusted under 35 U.S.C. 154(b) by 193 days.

(21) Appl. No.: 15/579,678

(22) PCT Filed: Jun. 3, 2016

(86) PCT No.: PCT/US2016/035691
§ 371 (c)(1),
(2) Date: Dec. 5, 2017

(87) PCT Pub. No.: WO2016/196911
PCT Pub. Date: Dec. 8, 2016

(65) Prior Publication Data
US 2018/0136187 A1 May 17, 2018

Related U.S. Application Data

(60) Provisional application No. 62/171,586, filed on Jun. 5, 2015.

(51) Int. Cl.
*G01N 33/18* (2006.01)
*G01N 30/88* (2006.01)
(Continued)

(52) U.S. Cl.
CPC ......... *G01N 33/1826* (2013.01); *G01N 30/08* (2013.01); *G01N 30/30* (2013.01);
(Continued)

(58) Field of Classification Search
CPC ........................... G01N 33/1826; G01N 30/88
See application file for complete search history.

(56) References Cited

U.S. PATENT DOCUMENTS

| 4,230,464 A | 10/1980 | Bonmati et al. |
| 4,895,017 A | 1/1990 | Pyke et al. |

(Continued)

FOREIGN PATENT DOCUMENTS

| DE | 2732762 | 3/1979 |
| DE | 102011007768 A1 | 10/2012 |

(Continued)

OTHER PUBLICATIONS

Lu, Chia-Jung et al. "A Dual-Adsorbent Preconcentrator for a Portable Indoor-VOC Microsensor System", Anal. Chem., vol. 73, No. 14, Jul. 15, 2001, pp. 3449-3457.

(Continued)

*Primary Examiner* — Eric S. McCall
*Assistant Examiner* — Timothy P Graves
(74) *Attorney, Agent, or Firm* — Renner, Otto, Boisselle & Sklar, LLP

(57) ABSTRACT

An analysis system includes a volatile organic compound (VOC) detection assembly enclosed in a housing assembly and configured to detect VOCs in a liquid. A thermal control assembly is disposed in the housing assembly and is configured to circulate air enclosed within the housing assembly and control an interior temperature of the housing. The VOC analysis system may be controlled to periodically conduct a VOC detection process. The thermal control assembly may (Continued)

be controlled to circulate air enclosed within the housing assembly and control the temperature of the enclosed air.

17 Claims, 11 Drawing Sheets

(51) Int. Cl.
    *G01N 30/08*         (2006.01)
    *G01N 30/30*         (2006.01)
    *G01N 30/02*         (2006.01)
    *G01N 30/06*         (2006.01)

(52) U.S. Cl.
    CPC ....... *G01N 30/88* (2013.01); *G01N 2030/025* (2013.01); *G01N 2030/062* (2013.01); *G01N 2030/884* (2013.01)

(56) References Cited

U.S. PATENT DOCUMENTS

| | | |
|---|---|---|
| 5,151,110 A | 9/1992 | Bein et al. |
| 5,258,171 A | 11/1993 | Eltomi |
| 5,289,715 A | 3/1994 | Staples et al. |
| 5,426,300 A | 6/1995 | Voss et al. |
| 5,492,838 A | 2/1996 | Pawliszyn |
| 5,625,139 A | 4/1997 | Stormbom |
| 5,807,426 A | 9/1998 | Ohtsuki et al. |
| 5,880,552 A | 3/1999 | McGill et al. |
| 5,917,135 A | 6/1999 | Michaels et al. |
| 5,920,143 A | 7/1999 | Tarui et al. |
| 6,074,461 A | 6/2000 | Wilson |
| 6,085,576 A | 7/2000 | Sunshine et al. |
| 6,134,944 A | 10/2000 | Yu et al. |
| 6,234,006 B1 | 5/2001 | Sunshine et al. |
| 6,244,096 B1 | 6/2001 | Lewis et al. |
| 6,295,861 B1 | 10/2001 | Tom et al. |
| 6,319,724 B1 | 11/2001 | Lewis et al. |
| 6,387,329 B1 | 5/2002 | Lewis et al. |
| 6,418,783 B2 | 7/2002 | Sunshine et al. |
| 6,422,061 B1 | 7/2002 | Sunshine et al. |
| 6,455,319 B1 | 9/2002 | Lewis et al. |
| 6,467,333 B2 | 10/2002 | Lewis et al. |
| 6,566,983 B2 | 5/2003 | Shin |
| 6,610,367 B2 | 8/2003 | Lewis et al. |
| 6,631,333 B1 | 10/2003 | Lewis et al. |
| 6,658,915 B2 | 12/2003 | Sunshine et al. |
| 6,684,683 B2 | 2/2004 | Potyrailo et al. |
| 6,691,702 B2 | 2/2004 | Appel et al. |
| 6,703,241 B1 | 3/2004 | Sunshine et al. |
| 6,759,010 B2 | 7/2004 | Lewis et al. |
| 6,772,513 B1 | 8/2004 | Frye-Mason et al. |
| 6,837,095 B2 | 1/2005 | Nakayama et al. |
| 6,841,391 B2 | 1/2005 | Lewis et al. |
| 6,870,234 B2 | 3/2005 | Brewer et al. |
| 6,883,364 B2 | 4/2005 | Sunshine et al. |
| 6,890,715 B1 | 5/2005 | Lewis et al. |
| 6,914,220 B2 | 7/2005 | Tian et al. |
| 6,914,279 B2 | 7/2005 | Lu et al. |
| 6,962,675 B2 | 11/2005 | Lewis et al. |
| 6,981,947 B2 | 1/2006 | Melker |
| 7,047,792 B1 | 5/2006 | Bhethanabotla et al. |
| 7,052,468 B2 | 5/2006 | Melker et al. |
| 7,052,854 B2 | 5/2006 | Melker et al. |
| 7,066,985 B2 | 6/2006 | Deane et al. |
| 7,078,237 B1 | 7/2006 | Mowry et al. |
| 7,089,780 B2 | 8/2006 | Sunshine et al. |
| 7,104,963 B2 | 9/2006 | Melker et al. |
| 7,122,152 B2 | 10/2006 | Lewis et al. |
| 7,135,059 B2 | 11/2006 | Deane et al. |
| 7,141,446 B2 | 11/2006 | Brewer et al. |
| 7,144,553 B2 | 12/2006 | Lewis et al. |
| 7,147,695 B2 | 12/2006 | Mitra |
| 7,153,272 B2 | 12/2006 | Talton |
| 7,168,298 B1 | 1/2007 | Manginell et al. |
| 7,189,353 B2 | 3/2007 | Lewis et al. |
| 7,194,891 B2 | 3/2007 | Tuller et al. |
| 7,282,676 B1 | 10/2007 | Bouchier et al. |
| 7,299,711 B1 | 11/2007 | Linker et al. |
| 7,399,449 B1 | 7/2008 | Oborny et al. |
| 7,430,928 B2 | 10/2008 | Grate et al. |
| 9,766,215 B2 | 9/2017 | Hassan et al. |
| 2002/0073764 A1 | 6/2002 | Guerra et al. |
| 2003/0115770 A1 | 6/2003 | Harano |
| 2005/0226773 A1 | 10/2005 | Liu |
| 2005/0289351 A1 | 12/2005 | England et al. |
| 2006/0088445 A1 | 4/2006 | Lewis et al. |
| 2006/0130611 A1 | 6/2006 | Lynn |
| 2006/0210425 A1 | 9/2006 | Mirkarimi |
| 2007/0062255 A1 | 3/2007 | Talton |
| 2007/0085446 A1 | 4/2007 | Chen |
| 2008/0289397 A1 | 11/2008 | Hassan et al. |
| 2010/0018288 A1 | 1/2010 | Yamanaka |
| 2010/0180667 A1 | 7/2010 | Bender et al. |
| 2015/0143872 A1* | 5/2015 | Hassan ................ G01N 29/022 73/23.4 |
| 2017/0038346 A1* | 2/2017 | Shreve .................. G01N 30/30 |

FOREIGN PATENT DOCUMENTS

| | | | |
|---|---|---|---|
| DE | 102011107715 A1 | 1/2013 | |
| EP | 2005108975 A1 | 11/2005 | |
| EP | 2546645 | * 1/2013 | ............ G01N 30/30 |
| EP | 1749206 B1 | 7/2014 | |
| GB | 2279740 | 1/1995 | |
| JP | 2234507 | 9/1990 | |
| WO | 9631773 | 10/1996 | |
| WO | 2005066288 | 7/2005 | |
| WO | 2013036760 A1 | 3/2013 | |

OTHER PUBLICATIONS

Siegal, M.P. et al., "Nannporous Carbon Films for Gas Microsensors", Langmuir, vol. 20, 2004, pp. 1194-1198.

Groves, W.A. et al., "Analyzing Organic Vapors in Exhaled Breath Using a Surface Acoustic Wave Sensor Array with Preconcentration: Selection and Characterization of the Preconcentrator Adsorbent", Analytica Chimica Acta, vol. 371, 1998, pp. 131-143.

Matney, M.L. et al., "Multisorbent Tubes for Collecting Volatile Organic Compounds in Spacecraft Air", AIHAJ, vol. 61, Jan./Feb. 2000, pp. 69-75.

M.P. Siegal et al., "Nanoporous-Carbon Adsorbers for Chemical Microsensors," Sandia Report, SAND2004-5277, Nov. 2004, 35 pages.

M.P. Siegal and W.G. Yelton, "Nanoporous-Carbon Coatings for Gas-Phase Chemical Microsensors," Advances in Science and Technology, vol. 48, 2006, pp. 161-168.

M.P. Siegal et al., "Nanoporous-carbon films for microsensor preconcentrators," Appl. Phys. Lett., vol. 80, No. 21, May 27, 2002, pp. 3940-3942.

Curtis D. Mowry et al., "Real-time Discriminatory Sensors for Water Contamination Events: LDRD 52595 Final Report," Oct. 2005, 57 pages.

Curtis D. Mowry et al., "Recent Advancements Toward Field Portable Detection of THMs by Surface Acoustic wave Detection," Mar. 2007, 27 pages.

Curtis D. Mowry et al., "Portable Field System for Rapid, On-Site Detection of Disinfection Byproducts in Water," Nov. 2005, 26 pages.

Tenax TA Adsorbent Resin Physical Properties, accessed Apr. 8, 2008, http://www.sisweb.com/index/referenc/tenaxtam.htm, 3 pages.

Inficon Hapsite Situprobe, 2007, 2 pages.

C. Eric Boswell, "Fast and Efficient Volatiles Analysis by Purge and Trap GC/MS," 1999, 5 pages.

Surface acoustic wave, accessed Apr. 8, 2008, http://en.wikipedia.org/wiki/Surface_acoustic_wave, 2 pages.

Acoustic Wave Technology Sensors, Drafts, Oct. 2000 http://www.sensorsmag.com/articles/1000/68/main.shtml, 13 pages.

(56) References Cited

OTHER PUBLICATIONS

PCT/US2016/035691; PCT International Search Report and Written Opinion of the International Searching Authority dated Aug. 1, 2016.
PCT/US2016/035691; Second Written Opinion of the International Searching Authority dated May 10, 2017.
PCT/US2016/035691; PCT International Preliminary Report on Patentability dated Aug. 25, 2017.

\* cited by examiner

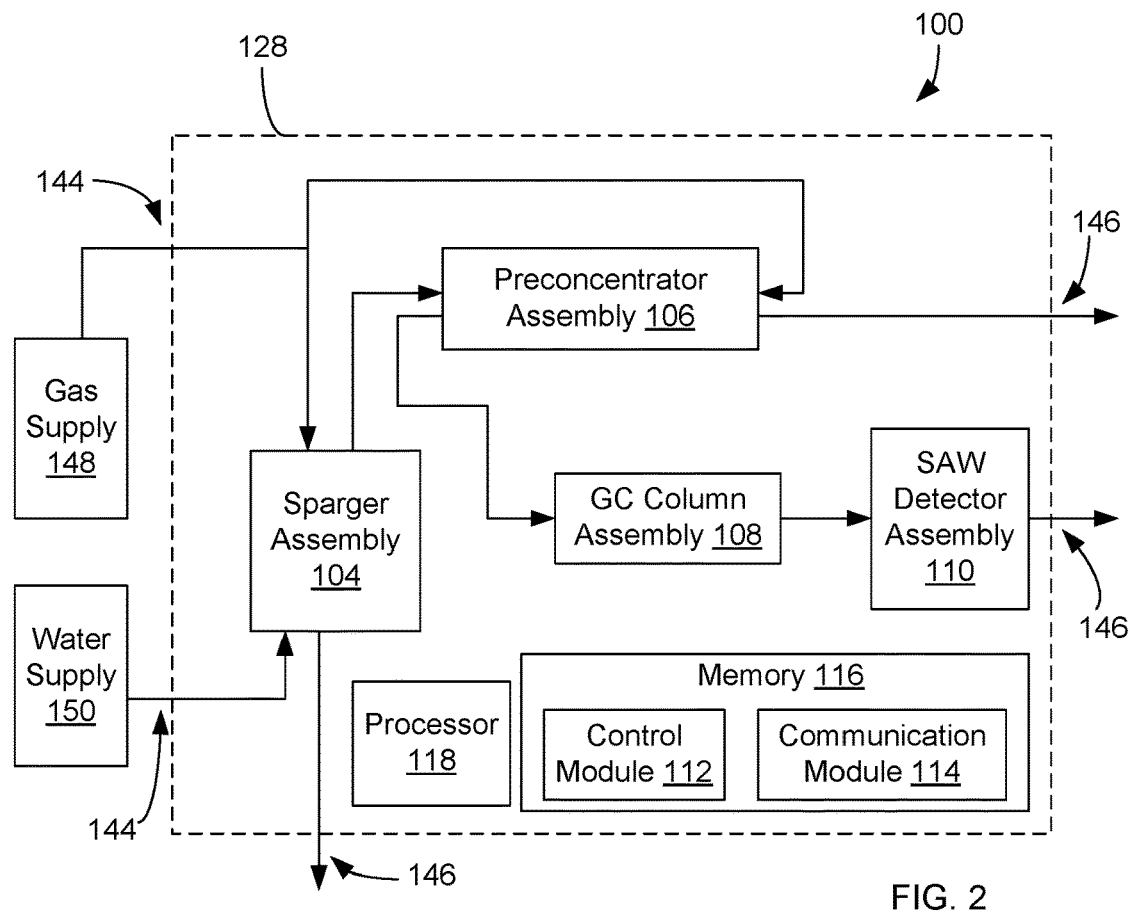
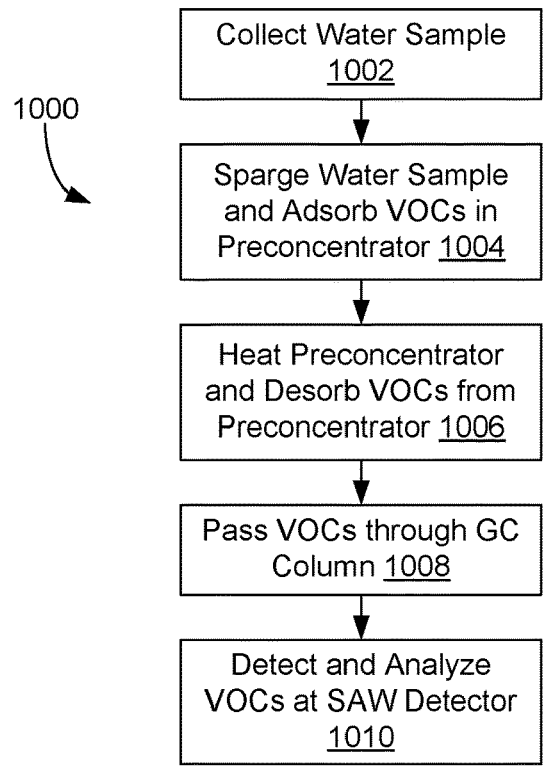
FIG. 2
FIG. 3

ANALYSIS SYSTEM AND METHOD FOR DETECTING VOLATILE ORGANIC COMPOUNDS IN LIQUID

RELATED APPLICATIONS

This application is a national phase of International Application No. PCT/US2016/035691 filed Jun. 3, 2016 and published in the English language and which claims the benefit of U.S. Provisional Application No. 62/171,586 filed Jun. 5, 2015, the disclosures of which are incorporated herein by reference in their entireties.

FIELD OF INVENTION

The present disclosure relates to chemical analysis systems and methods, and in particular to an analysis system and method for detecting volatile organic compounds in a liquid.

BACKGROUND

Detection of the presence/amount of volatile organic compounds (VOCs) in a liquid (e.g., water such as drinking water) is typically conducted in a laboratory setting using one or more laboratory instruments. As an example, in a typical analysis method conducted in a laboratory, the VOCs are extracted from the water sample matrix using a technique such as liquid-liquid extraction, purge and trap, or membrane separation. These VOCs can then be introduced into a gas chromatograph (GC) column and then to a detector such as a mass spectrometer, surface acoustic wave (SAW) detector, flame ionization detector (FID), or electron capture detector (ECD).

Reliability and accuracy issues may be present with these analysis methods, particularly in view of the testing environment in which the analysis method is carried out. For example, the conditions of the water sample and the testing environment should consistently be as close as possible to ideal conditions (which may be the conditions at which the analysis system is calibrated) to allow the analyzers and instruments associated with the analysis system to accurately identify and quantify the VOCs. While the laboratory setting can provide these testing conditions, the analysis of remotely-located sources of liquid at a location outside of the laboratory can be an issue, particularly in situations where it is desired to repeatedly monitor the remotely-located source of liquid.

SUMMARY OF INVENTION

The present invention provides improvements in chemical analysis systems and methods and, in particular, improvements in the reliability and/or accuracy of on-site VOC detection/analysis of remotely-located sources of liquid.

Environmental conditions at the remotely-located source of liquid are often not ideal for VOC analysis. For example, the accuracy of VOC measurements can vary considerably as a function of temperature. The analysis system may be calibrated at a given temperature, but ambient temperature can vary considerably in remote location environments outside of the laboratory. Wide temperature swings can occur over a 24 hour period and from season to season at a given location. Because of their volatile nature, the amount of VOC compounds extracted from the water sample (e.g., during gas sparging) may be dependent on the sample water temperature. Substantial changes in ambient temperature can also shift compound retention times from the original calibration and may cause compound concentrations to be either misidentified or missed entirely. Hence, measurement accuracy may degrade as the sample water temperature varies from the calibration temperature. In addition, cold sections inside the analysis system can cause the moisture rich stream of carrier gas from the sparger to condense into water droplets inside the gas pathways or in the sorbent bed of the trap, creating flow problems, damaging valves, and causing excessive moisture to reach the GC column and the detector.

In addition to temperature, other factors can have a negative effect on the reliability/accuracy of the analysis. High humidity in damp locations can condense into water on components of the analysis system. Dust, insects, and other pests may also be present and may interfere with components of the analysis system. High concentrations of corrosive chlorine from water treatment processes may be present in the air and may come into contact with components of the analysis system. Each of these factors may compromise the components of the analysis system and/or the analysis results.

The analysis system of the present disclosure provides an isolated environment (e.g., sealed enclosure) that may address one or more of these varied environmental challenges, thereby improving the reliability and/or accuracy of on-site VOC detection/analysis. The analysis system of the present disclosure may also protect the components of the analysis system from atmospheric conditions such as humidity, condensation, and corrosive vapors; and from other considerations such as dust, insects, and pests. This isolated environment would conventionally present thermal management issues due to the heat produced by components of the analysis system such as the control and communication electronics, the heated preconcentrator, the heated GC column, and the heated sparging assembly. But the thermal management provided by the analysis system of the present disclosure may allow for a relatively consistent testing temperature. The thermal management provided by the analysis system of the present disclosure may also minimize any effect from heat transfer between the isolated environment and the ambient environment present at the location of the analysis system. In addition, one or more components within the analyzer analysis system may be optimized to work more effectively within the thermal system.

According to one aspect of the invention, an analysis system includes: a housing assembly defining an enclosure; a volatile organic compound detection assembly enclosed in the enclosure of the housing assembly, the volatile organic compound detection assembly configured to detect a volatile organic compound in a liquid; and a thermal control assembly enclosed in the enclosure of the housing assembly, the thermal control assembly configured to circulate air enclosed within the housing assembly and control a temperature of the enclosed air.

The thermal control assembly may include a heat exchanger assembly, the heat exchanger assembly including: a plurality of core plates; and a cooling tube having its length partially disposed between the core plates, a first portion of the cooling tube extending from the core plates and coupled an input of the housing assembly configured to input liquid from the liquid source external to the housing, a second portion of the cooling tube extending from the core plates and coupled to an output configured to output from the housing assembly the liquid passing through the cooling tube.

One or more of a water pump, pressure regulator, and a water chiller may be external to the housing assembly and coupled to the input, the liquid source coupled to the input through the one or more of the water pump, pressure regulator, and water chiller.

The heat exchanger assembly may further include a finned plate coupled to one of the core plates.

The heat exchanger assembly may further include at least one heating element.

The heating element may be disposed between one of the core plates and the finned plate.

The analysis system may further include a backplate to which at least a portion of the volatile organic compound detection assembly is mounted, the backplate enclosed in the housing and arranged in a central or offset location to provide an air gap on each side of the backplate, the heat exchanger mounted to an opposite side of the backplate to which the at least a portion of the volatile organic compound detection assembly is mounted.

The backplate may include cutouts at top and bottom locations of the backplate, each cutout providing an air passage between the air gaps.

The thermal control assembly may include a fan configured to circulate the air enclosed within the housing.

The fan may be proximate the heat exchanger assembly and may be arranged to output at least a portion of the circulating air in the direction of and over the surface of the heat exchanger assembly.

The thermal control assembly may further include an air focusing duct disposed between the fan and the heat exchanger assembly, the air focusing duct configured to focus the air output by the fan in the direction of and over the surface of the heat exchanger assembly.

The housing may not include a fan or vent connecting the enclosure of the housing assembly to an ambient environment in which the analysis system is located.

The analysis system may further include a backplate to which at least a portion of the volatile organic compound detection assembly is mounted, the backplate enclosed in the housing and arranged in a central or offset location to provide an air gap on each side of the backplate.

The backplate may include cutouts at top and bottom locations of the backplate providing an air passage between and fluidly connecting the air gaps.

The thermal control assembly may include a fan configured to circulate the air enclosed within the housing.

The fan may be located in one of the air gaps located proximate a first side of the backplate, and a second fan may be located in another of the air gaps proximate a second side of the backplate.

The fan and the second fan may be respectively arranged to output air in opposite directions and establish air circulation within the housing assembly.

The analysis system may further include insulation at one or more internal walls of the housing assembly.

The housing assembly may include a removable cover, and the cover may include an o-ring configured to mate against a face of the main housing body.

The volatile organic compound detection assembly may be embodied as a purge and trap gas chromatography system.

The volatile organic compound detection assembly may include a sparger assembly configured to retain a liquid sample and sparge VOCs from the liquid sample.

The sparger assembly may include a container and a heater at an outside surface of the container.

The volatile organic compound detection assembly may include a preconcentrator assembly configured to adsorb volatile organic compounds passing therethrough and desorb the adsorbed volatile organic compounds for analysis.

The preconcentrator may include a tubular preconcentrator including a sorbent bed disposed therein and a preconcentrator heater around the preconcentrator.

The preconcentrator assembly may include a preconcentrator fan configured to direct the air circulating in the housing assembly into contact with the preconcentrator assembly.

The volatile organic compound detection assembly may include a gas chromatograph column assembly configured to separate volatile organic compounds passed therethrough.

The gas chromatograph column assembly may include a gas chromatograph column and a gas chromatograph column heater.

The volatile organic compound detection assembly may include a surface acoustic wave detector configured to detect a mass of organic compounds separated by a gas chromatograph column.

The analysis system may further include a control module configured to control operation of the volatile organic compound detection assembly and control operation of the thermal control assembly, electronics associated with the control module enclosed within a Faraday cage within the housing assembly.

According to another aspect of the invention, a method of detecting a volatile organic compound in a liquid sample includes: conducting a volatile organic compound detection process by controlling a volatile organic compound detection assembly, the volatile organic compound detection assembly enclosed within a housing assembly, the housing assembly including an input for inputting the liquid from a liquid source external to the housing assembly; and controlling a thermal control assembly enclosed in the housing assembly to circulate air enclosed within the housing assembly and control the temperature of the enclosed air.

The volatile organic compound detection process may include: sparging a liquid sample with a sparging assembly; collecting the volatile organic compound with a preconcentrator assembly; desorbing the volatile organic compound from the preconcentrator assembly; separating the volatile organic compound as desorbed from the preconcentrator assembly with a gas chromatograph column assembly; and detecting the mass of the volatile organic compound separated by the gas chromatograph column assembly with a surface acoustic wave detector.

The control of the thermal control assembly may include control of a heat exchanger assembly enclosed in the housing assembly.

The control of the thermal control assembly may include: inputting liquid from a liquid source external to the housing assembly through a cooling tube that has a first portion extending from an input of the housing assembly to a plurality of core plates of the heat exchanger assembly, and outputting liquid through a second portion of the cooling tube extending from the core plates to an output of the housing assembly.

The control of the thermal control assembly may include detecting that the temperature of the enclosed air is above a predetermined temperature, and controlling the heat exchanger assembly to pass liquid from the liquid source through the cooling tube.

The method may further include controlling one or more of a water pump, pressure regulator, and a water chiller external to the housing assembly and coupled to the liquid source to control one or both of the temperature and pressure of the liquid input to the heat exchanger assembly.

The control of the thermal control assembly may further include controlling a heating element in physical contact with one of the core plates.

The control of the thermal control assembly may include detecting that the temperature of the enclosed air is below a predetermined temperature, and supplying electrical current to the at least one heating element of the heat exchanger assembly.

The control of the thermal control assembly may include operating a fan proximate the heat exchanger assembly to direct at least a portion of the circulating air in the direction of and over the surface of the heat exchanger assembly.

The control of the thermal control assembly may include operation of a fan within the housing assembly, the fan configured to circulate the air enclosed within the housing.

The fan may be controlled to continuously circulate the air within the housing.

The air may be circulated around a backplate enclosed in the housing assembly to which at least a portion of the volatile organic compound detection assembly is mounted, the backplate arranged in a central or offset location to provide an air gap on each side of the backplate and including cutouts at top and bottom locations of the backplate to fluidly connect the air gaps.

The fan may be located in one of the air gaps located proximate a first side of the backplate, and a second fan may be located in another of the air gaps proximate a second side of the backplate, the fans respectively arranged to output air in opposite directions and establish air circulation within the housing assembly.

According to another aspect of the invention, a housing assembly includes: a housing main body; a cover removably attached to the main body and enclosing an interior of the housing assembly from an ambient environment in which the analysis system is located; a backplate enclosed in the housing main body and arranged in a central or offset location therein to provide an air gap on each side of the backplate, the backplate including cutouts at top and bottom locations of the backplate, each cutout providing an air passage between the air gaps; a fan enclosed in the housing main body and configured to circulate the air enclosed within the housing assembly; and a heat exchanger assembly enclosed in the housing main body.

The heat exchanger assembly may include: a plurality of core plates; and a cooling tube having its length partially enclosed between the core plates, a first portion of the cooling tube extending from the core plates and coupled an input of the housing assembly configured to input liquid from a liquid source external to the housing, a second portion of the cooling tube extending from the core plates and coupled to an output of the housing assembly configured to output from the housing assembly the liquid passing through the cooling tube.

The heat exchanger assembly may further include at least one heating element.

The heat exchanger assembly may further include a finned plate coupled to one of the core plates.

The heating element may be disposed between one of the core plates and the finned plate.

The heat exchanger assembly may be mounted to the backplate.

The fan may be proximate the heat exchanger assembly and arranged to output at least a portion of the circulating air in the direction of and over the surface of the heat exchanger assembly.

The housing assembly may further include an air focusing duct disposed between the fan and the heat exchanger assembly, the air focusing duct configured to focus the air output by the fan in the direction of and over the surface of the heat exchanger assembly.

The fan may be located in one of the air gaps located proximate one side of the backplate, and a second fan may be located in another of the air gaps proximate an opposite side of the backplate.

The fans may be respectively arranged to output air in opposite directions and establish air circulation within the housing assembly.

The housing assembly may further include insulation at one or more internal walls of the housing assembly.

The cover may include an o-ring configured to mate against a face of the main housing body.

The foregoing and other features of the invention are hereinafter described in greater detail with reference to the accompanying drawings.

BRIEF DESCRIPTION OF THE DRAWINGS

FIG. 2 is a schematic illustration of an exemplary analysis system in accordance with the present disclosure.

FIG. 3 is a schematic flow diagram of an exemplary analytical process performed by the exemplary analysis system in accordance with the present disclosure.

DETAILED DESCRIPTION

Figure 1:
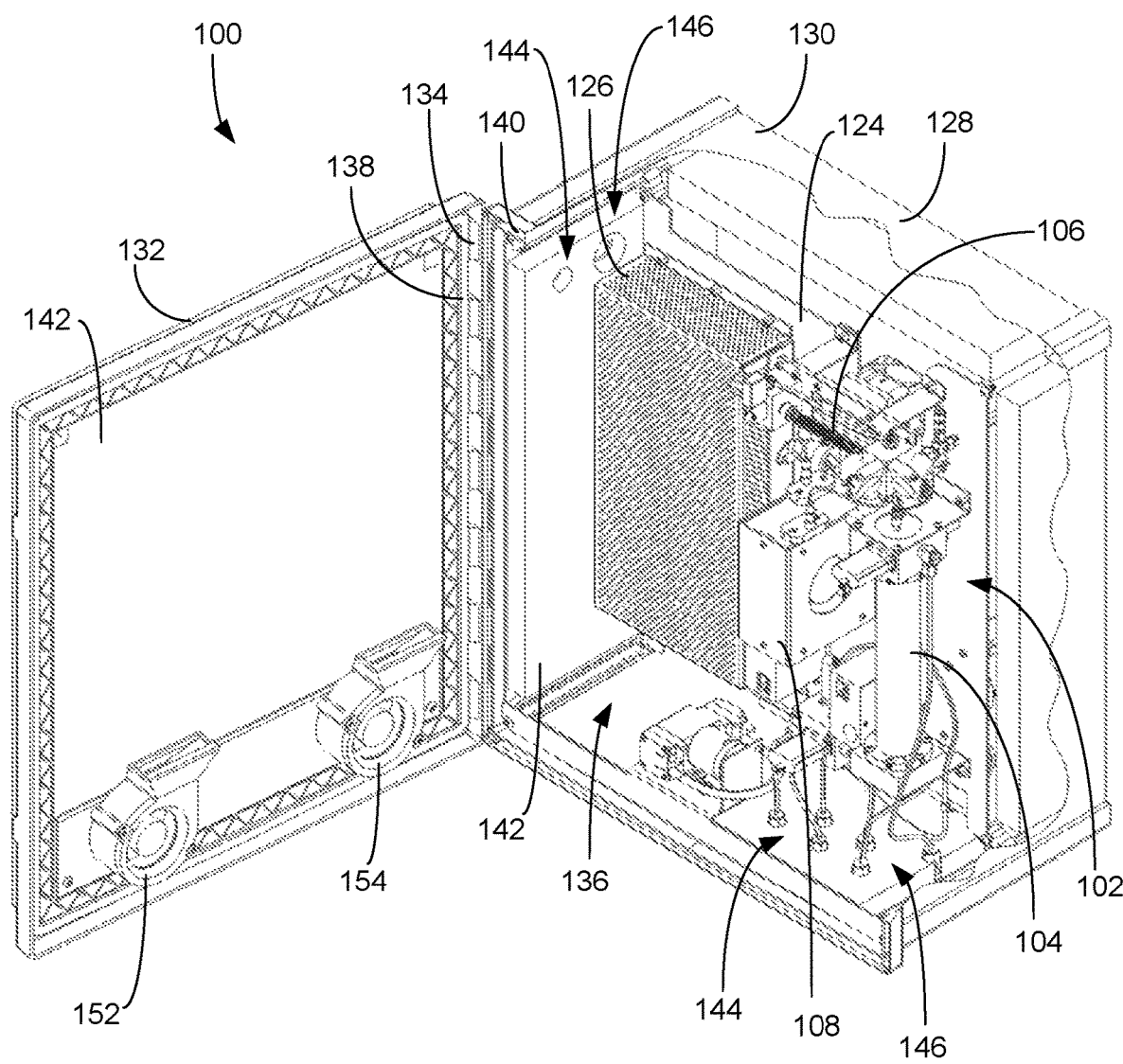
FIG. 1 is a schematic perspective illustration of an exemplary analysis system in accordance with the present disclosure.
Figure 4:
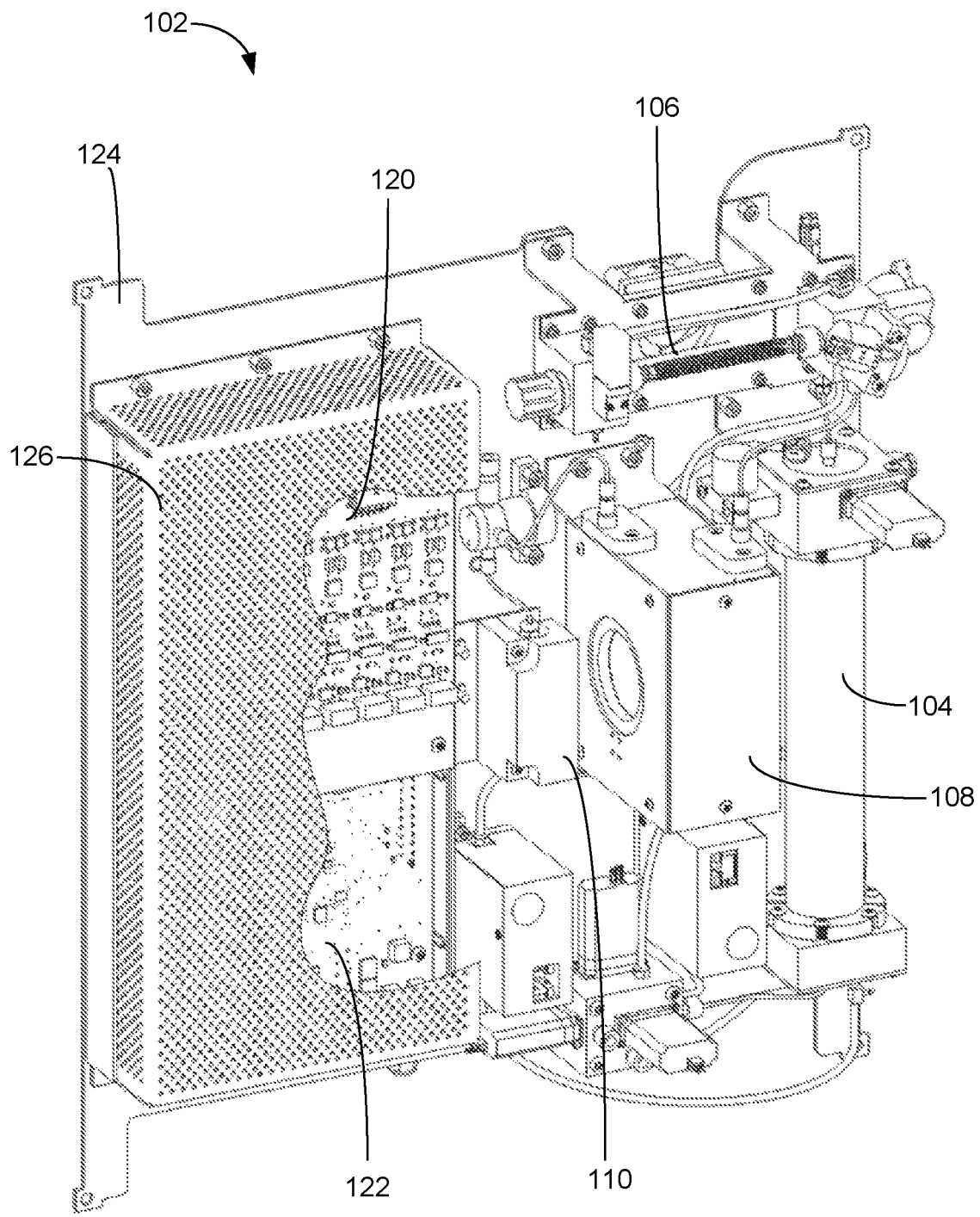
FIG. 4 is a schematic perspective illustration of components of an exemplary analysis system in accordance with the present disclosure.

Referring now to the drawings in detail and initially to FIGS. 1, 2, and 4, an exemplary analysis system according to the invention is indicated generally by reference numeral 100. The analysis system 100 has particular application as a system for detecting one or more VOC compounds in water and will be chiefly described in this context. In one example, the system 100 is suitable for detecting trihalomethane (THM) chemical compounds in drinking water. It should be understood, however, that this is an exemplary application of the analysis system 100 and an analysis system according to the present disclosure may have other applications as well, such as the analysis of other organic compounds in water or other liquids. Furthermore, as described herein, the analysis system 100 may enable the on-site VOC detection/analysis of remotely-located sources of liquid. It should be understood, however, that the analysis system 100 may be utilized in any suitable environment, including a laboratory environment.

The analysis system 100 includes a VOC detection assembly 102 embodied as an integrated purge and trap gas chromatography system. As shown, the VOC detection assembly 102 generally includes a sparger assembly 104, a preconcentrator assembly 106, a GC column assembly 108, and a SAW detector assembly 110. As schematically shown in FIG. 2, the sparger assembly 104, preconcentrator assembly 106, GC column assembly 108, and SAW detector assembly 110 may be in fluid communication via flow paths through the analysis system 100, such as through manifolds, conduits, tubes, and the like. Fluid flow (e.g., liquid and/or gas flow) in the VOC detection assembly 102 may be effectuated by valves, pumps, solenoids, and the like. The various components of the VOC detection assembly 102 are discussed in more detail below.

The analysis system 100 may include electronics to effectuate overall operation of the system. In the embodiment shown, the analysis system 100 includes a control module 112 and a communications module 114 (FIG. 2). The control module 112 may control the functions and overall operation of the analysis system 100 (e.g. operation of valves, pumps, signal processing, thermal management (heating and/or cooling), data collection, data analysis, data output, and the like). As an example, components of the analysis system 100 (e.g., the VOC detection assembly 102) may be controlled by the control module 112 to perform an analytical process for detecting VOCs in water. In some embodiments, this analytical analysis process may include purging VOCs of interest from a water sample contained in the sparger assembly 104, collecting and desorbing the VOCs in the preconcentrator assembly 106, separating the VOCs via the GC column assembly 108, and detecting the VOCs using the SAW detector assembly 110. As another example, components of the analysis system 100 may be controlled by the control module 112 to provide thermal management within the housing assembly.

The communications module 114 may provide communication with an external device (not shown), such as an external computer, a plant facility control system, and the like. In some embodiments, the external device may be located at the location of the analysis system 100. In other embodiments, the external device may be located at a remote location with respect to the analysis system 100. Exemplary communication protocols that may be utilized by the communication module include analog 4-20 mA or digital protocols such as Profibus, Modbus, Ethernet/IP, and the like.

The functions of the control module 112 and/or the communication module 114 may be provided by one or more programs stored in one or more non-transitory computer readable medium (e.g., a memory 116) and executed by one or more processors (e.g., processor 118) associated with the control module 112 and/or communications module 114. With exemplary reference to FIG. 4, functionality of the control module 112 and/or communications module 114 may be realized by one or more of interface boards 120, 122. For example, the one or more programs providing the control module 112 and/or communications module 114 may be stored on one or more memories on the one or more of interface boards 120, 122 and may be executed by one or more processors on the one or more of interface boards 120, 122.

With specific reference to FIG. 4, components of the VOC detection assembly 102 and one or more of interface boards 120, 122 may be mounted to a backplate 124. The backplate 124 may allow the components to be more easily assembled outside of the enclosure before being mounted in the housing assembly 128. As described in more detail below, the backplate may be positioned in the housing of the analysis system in a position that helps to facilitate the circulation of air within the housing.

In some embodiments, the control module 112 and/or the communication module 114 (e.g., interface boards 120, 122) are housed within a faraday cage 126. The faraday cage 126 may be mounted to the backplate and may enclose the one or more interface boards 120, 122. The electronics associated with the one or more interface boards 120, 122 may generate heat within the analysis system (e.g., within the housing). However, the faraday cage 126 may contribute to the thermal management by enclosing the electronics and providing perforations on one or more of its surfaces. The perforations of the faraday cage may control electromagnetic compatibility (EMC) emissions while also allowing substantial convective transfer of waste heat from the one or more of interface boards 120, 122. This may help to minimize the electronics steady state operating temperature. In other embodiments, the analysis system 100 does not include a faraday cage. Accordingly, the one or more interface boards 120, 122 may be directly exposed to the interior of the housing assembly 128.

Although not specifically shown, a display may be coupled to one or more of the interface boards 120, 122 for presenting information to a user (e.g. analysis data). A user interface may also be included that allows the user to interact with the analysis system 100. The display and the user interface may be used in conjunction with one another to implement a touch screen associated with the display. One or more input/output (I/O) interface(s), such as a USB interface, may couple the one or more of interface boards 120, 122 to another device (e.g., a computer) or an accessory (e.g., a printer) via a cable.

The sparger assembly 104, preconcentrator assembly 106, GC column assembly 108, SAW detector assembly 110, and interface boards 120, 122 may be mounted to the backplate 124 and housed within an enclosure 136 defined by a housing assembly 128. With additional reference to FIG. 5, the housing assembly 128 defines an enclosure 136 and may include a main housing body 130 and a cover 132. In the embodiment shown, the cover 132 is embodied as a door attached to the main housing body 130 via a hinge 134 (e.g., a piano hinge). In other embodiments (not shown), the cover 132 may be removably attached to the main housing body 130 by mechanical fastening members such as one or more latches, one or more screws, and the like. The housing cover 132 permits access to the interior (enclosure 136) of the main housing body 130. The housing assembly 128 may be made of any suitable material. In some exemplary embodiments, the housing assembly 128 (e.g., main housing body 130 and/or cover 132) may be made from a plastic/polymeric material such as polypropylene. In other embodiments, the housing assembly 128 (e.g., main housing body 130 and/or cover 132) may be made from a metal or metal alloy. The use of a metal or metal alloy housing assembly may aid in the control of EMC emissions.

In some embodiments, the housing assembly 128 includes one or more features that may isolate the components disposed therein from the external environment. In an example, the housing cover 132 includes an o-ring 138 that may mate against the front face 140 of the main housing body 130 when closed, and which may form a dust and/or water tight seal. In another example, one or more layers of thermal insulation 142 may be attached to the interior surfaces of the main housing body 130 and to the interior surface of the housing cover 132. The thermal insulation may reduce the amount of heat transferred between the enclosure 136 of the housing assembly 128 and the ambient environment that is external to the housing assembly 128.

In some embodiments, the housing assembly 128 includes one or more inputs 144 and/or outputs 146. As described above, the housing assembly 128 may isolate the components disposed therein from the external environment. The one or more inputs 144 and/or outputs 146 may allow for the ingress into and/or the egress from the enclosure 136 of the housing assembly 128. The one or more inputs 144 and/or outputs 146 may include, for example, a liquid sample input, a liquid sample output, an electric power input, one or more electrical connections, a communications input, a communications output, a supply gas input, a gas exhaust, a cooling liquid input, a cooling liquid output, and/or the like.

In an example, a gas supply 148 (FIG. 2) may be coupled to the VOC detection assembly 102 through one or more of the inputs 144 for supplying carrier gas. The carrier gas may be any suitable carrier gas, for example, helium, nitrogen, argon, hydrogen, and/or air. Upon passing through one or more components of the VOC detection assembly 102, the carrier gas may be output from the analysis system 100 via one or more of the outputs 146. In another example, a water supply 150 (FIG. 2) may be coupled to the sparger assembly 104 through one or more of the inputs 144 for supplying the water supply. Water input to the sparger assembly 104 may subsequently be output from the analysis system 100 via one or more of the outputs 146.

FIG. 3 is a flow diagram of an exemplary analytical process 1000 performed by the exemplary analysis system 100 in accordance with the present disclosure. The exemplary analytical process 1000 may be performed using the integrated purge and trap gas chromatography system described herein. It will be understood, however, that the exemplary analytical process 1000 may be performed using a different analysis system housed within the housing assembly 128. Furthermore, it will be understood that in other embodiments, the analysis system 100 may perform a different analytical process.

Figure 6:
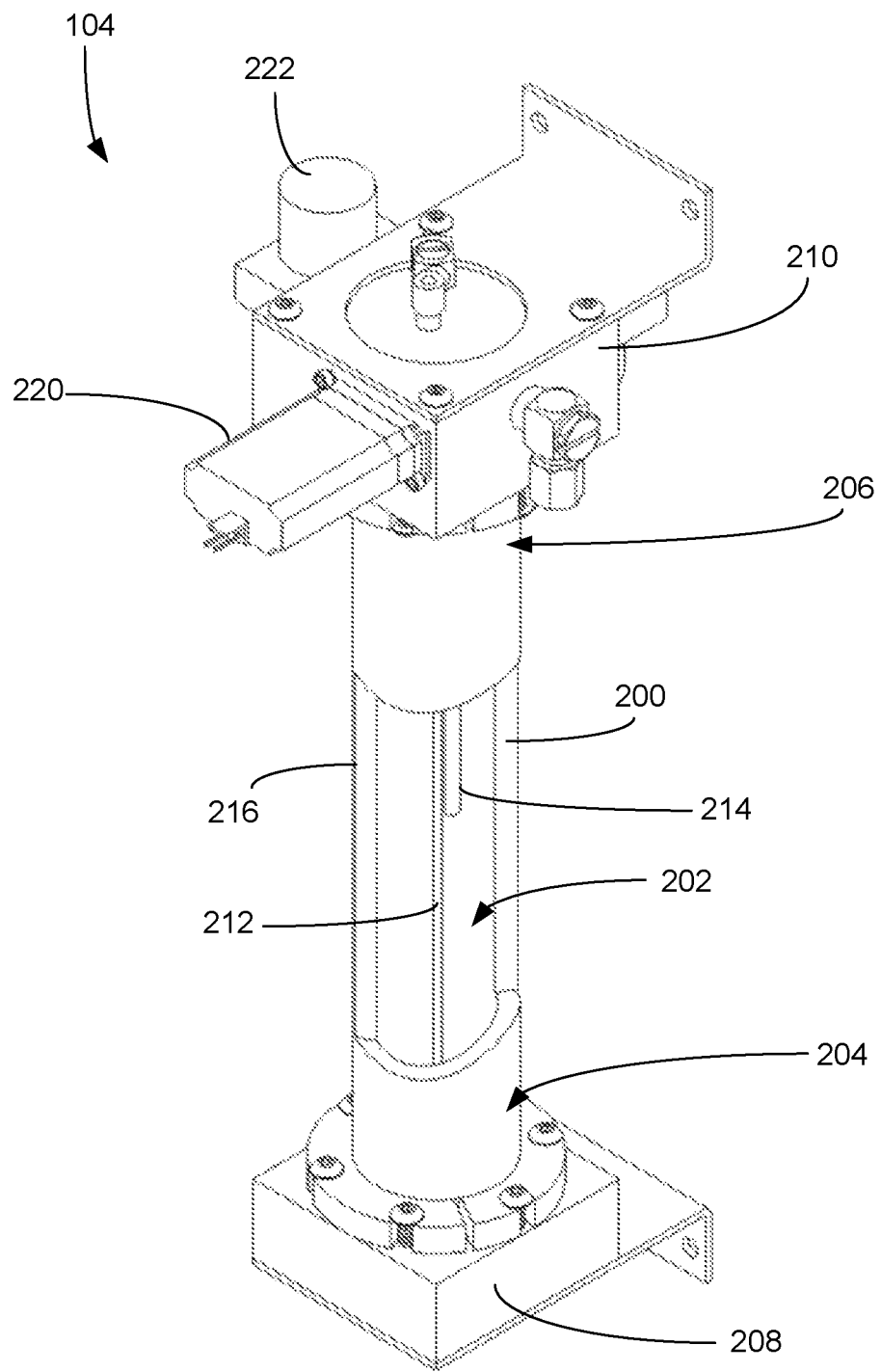
FIG. 6 is a schematic perspective illustration of an exemplary sparger assembly in accordance with the present disclosure.

At step 1002, a water sample is collected in the sparger assembly 104 for analysis. The sparger assembly may be configured to retain a liquid sample and sparge VOCs therefrom. Referring now to FIG. 6, the sparger assembly 104 includes a container 200 configured to hold a liquid for conducting a sparging process. In the embodiment shown, the container 200 is configured as a hollow body (e.g., a tubular member) surrounding an internal volume 202 and defining a longitudinal axis extending between a first end 204 and a second end 206. In some embodiments, the container 200 may be made of a material having a high thermal conductivity, such as a metallic material (e.g., copper). In other embodiments, the container 200 may be made of a material such as glass or a polymer. The container 200 may be configured to hold a prescribed amount of water (or other suitable sample liquid) from which the VOCs are to be purged.

The container 200 may be coupled to an inlet and drain valve manifold 208 at its first end 204 and may be coupled to a gas valve manifold 210 at its second end 206. The inlet and drain valve manifold 208 may be coupled to one of the inputs 144 of the housing assembly 128 and may be configured to direct water from the water supply 150 into the container 200 for testing. The inlet and drain valve manifold 208 may also be coupled to one of the outputs 146 of the housing assembly 128 and may be configured to dispose of the water sample from the container 200 after sparging. The gas valve manifold 210 may be coupled to one of the inputs 144 of the housing assembly 128 and may be configured to direct carrier gas from the gas source 148 to the water sample contained in the container 200 for sparging. The gas valve manifold 210 may also be coupled to the preconcentrator assembly 106 and may direct the sparge gas stream containing the VOCs from the water sample to the preconcentrator assembly 106. Operation of the sparger assembly 104 (e.g., operation of the drain valve manifold 208 gas valve manifold 210) may be provided by controlling one or more actuators, solenoids, pumps associated therewith (exemplified at 220 and 222 in FIG. 6). Control may be carried out by the control module 112.

A sparge tube 212 may be disposed in the container. As shown, the sparge tube 212 is configured as an open-ended hollow body defining a longitudinal axis that extends from the second end 206 of the container 200 toward the first end 204 of the container 200. The sparge tube 212 may be made from any suitable material (e.g., a metallic material such as stainless steel or copper, a polymeric material such as polyether ether ketone, or another suitable material), and may be any suitable size. In one example, the outer diameter of the sparge tube 212 may range from about 0.063 inches (0.16 cm) to about 0.125 inches (0.318 cm). The relatively small diameter of the sparge tube 212 minimizes the immersed surface area available on which bubbles can coalesce, thereby minimizing the lost efficiency associated with this coalescing effect.

The sparge tube 212 may be coupled to the gas valve manifold 210 at one end. The length of the sparge tube 212 is substantially the length of the container 200, such that the other end of the sparge tube 212 is proximate the first end of the container. In some embodiments, the end of the sparge tube 212 proximate the first end of the container may include a gas dispersal member (not shown) configured to distribute gas from the sparge tube 212. In embodiments where the container 200 is a tubular member, the dispersal member may have a diameter of approximately the inner diameter of the container 200 so that carrier gas bubbles emitted from the dispersal member may be distributed across the water sample contained in the container 200. The carrier gas may be carried via the sparge tube 212 to the first end 204 of the container 200 to produce the gas bubbles that extract the VOCs from the water sample as they pass through the water sample.

An overflow tube 214 may be positioned inside of the container 200 with its inlet set at a specific height from the first end 204 of the container 200. The overflow tube 214 may be coupled to the inlet and drain valve manifold 208 or to the gas valve manifold 210, with the manifold in-turn coupled to an outlet 146 of the housing assembly 128. Accordingly, the overflow tube 214 may allow the water sample to fill to the level of the inlet of the overflow tube 214 when the water sample is loaded into the container 200. Once this level is reached, any additional water flow into the container 200 may exit through the overflow tube 214. Using this approach, it is possible to specifically set the volume of the water sample by the height of the inlet to the overflow tube 214 relative to the bottom of the container. This may assure that a consistent volume of water sample will be collected each time the container 200 is filled. A consistent volume of water sample may improve the accuracy and repeatability of VOC concentration measurement. In one example, the overflow tube 214 may be positioned such that the water sample is provided at a prescribed volume of 40 mL. In other examples, the prescribed amount of water sample may be different, and the overflow tube may be positioned such that the water sample is provided at a different prescribed amount (e.g. in the range of 20 to 100 mL).

The length and diameter of the container 200 may be configured such that there is sufficient distance between the first end 204 of the container 200 and the inlet of the overflow tube 214; and such that there is sufficient distance between the inlet of the overflow tube 214 and the second end 206 of the container. This may ensure that there is sufficient purging of the VOCs from the liquid, and that there is sufficient travel distance from the water level in the container 200 to the second end 206 to allow water vapors to interact with each other and condense on the inner side wall of the container 200. In an example wherein the overflow tube 214 is arranged to provide a maximum of 40 mL of liquid, the level of liquid in the container 200 (e.g., the distance between the first end 204 and the inlet of the overflow tube 214) may be between 2.5 inches (6.35 cm) to 4 inches (10.16 cm), and the distance between the inlet of the overflow tube 214 and the second end 206 may be between 3.5 inches (8.89 cm) to 5 inches (12.7 cm).

In some embodiments, a heater 216 (e.g., a flexible membrane heater) may be attached to the outside surface of the container 200. The heater 216 may encircle a portion or the entire circumference of the container 200 and may cover a portion or the entire length of the container 200. Because the temperature of the water sample input to the container 200 may vary due to environmental conditions, the heater 216 may heat the water sample to a consistent testing temperature. As an example, in some environments, the water sample may be input to the container 200 at a temperature as low as about 0° C. The heater 216 may raise the temperature of the water sample to the testing temperature. In some embodiments, the testing temperature of the water sample may be in the range of 25° C. to 95° C. In other embodiments, the testing temperature of the water sample may be in the range of 25° C. to 50° C. By using a high thermal conductivity material for the container 200, the heat applied by the heater 216 may be more efficiently transferred to the water sample as compared with a material having a lower thermal conductivity. This may reduce the time required to heat the water sample, minimize the temperature increase of the container wall, and allow for more precise control of water sample temperature. Temperature control of the water sample may improve the accuracy and repeatability of VOC concentration measurement. For example, the analysis system 100 may be calibrated using a sample having a given temperature, and the sparger assembly 104 may control the temperature of the water sample to be tested to be within, for example ±5° C. of the calibration temperature. In other embodiments, the sparger assembly 104 may control the temperature of the water sample to be tested to be within, for example ±3° C. of the calibration temperature.

In other embodiments, the sparger assembly 104 may control the temperature of the water sample to be tested to be within, for example ±1° C. of the calibration temperature.

In some embodiments, although not specifically shown, a cooling jacket may be attached to the outside surface of the sparge tube. Similar to the heater, the cooling jacket may encircle a portion or the entire circumference of the container 200 and may cover a portion or the entire length of the container 200. In some examples, the cooling jacket may be integrated with the heater. The cooling jacket may provide further temperature control of the water sample by providing the ability to cool the water sample (e.g., in instances where the temperature of the water sample input to the container 200 is above the desired testing temperature.

Accordingly, the water sample may be input through the housing 128 via an input 144, may pass through the inlet and drain valve manifold 208, and may fill the container 200 to a predetermined level. The water sample may be input to the container 200 for a predetermined amount of time suitable for filling the container 200 to the predetermined level. During the filling, any excess sample water may be removed via the overflow tube 214. In some embodiments, once input to the container 200, the water sample may be heated or cooled to a desired testing temperature.

With continued reference to FIG. 3, at step 1004, the water sample is sparged and the VOCs are collected by the preconcentrator assembly 106. Carrier gas may be input through the housing 128 via an input 144, may pass through the gas valve manifold 210, and may be carried via the sparge tube 212 to the first end 204 of the container 200 to produce gas bubbles that flow through and extract the VOCs from the water sample. The carrier gas that has passed through the water sample and that includes the VOCs is again passed through the gas valve manifold 210 and to the preconcentrator assembly 106.

Figure 7:
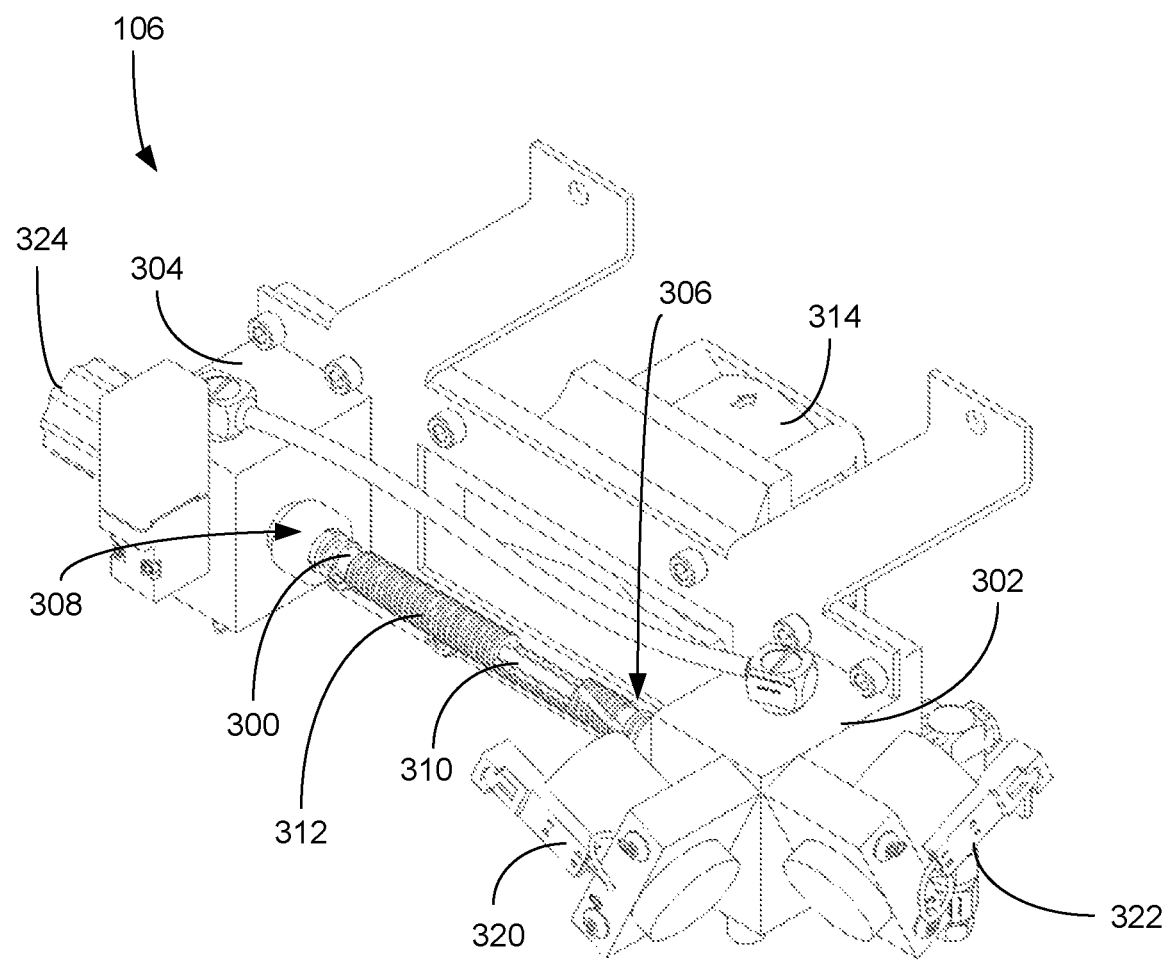
FIG. 7 is schematic perspective illustration of an exemplary preconcentrator assembly in accordance with the present disclosure.

Referring now to FIG. 7, the preconcentrator assembly 106 includes a preconcentrator 300 disposed between and coupled to a GC column valve manifold 302 and a preconcentrator vent valve manifold 304. The preconcentrator 300 may be configured as one or more metal tubular members of a suitable diameter and length that extend between a first end 306 and a second end 308. In one example, the outer diameter of a preconcentrator 300 may be less than about 0.20 inch (0.51 cm). In one example, the preconcentrator 300 may have a length of about 2 inches (5.1 cm) to about 6 inches (15.3 cm). A sorbent bed 310 is disposed in the preconcentrator 300 and may include one or more suitable adsorbing material such as fine mesh, commercial chemical adsorbent beads. For example, a sorbent bed 310 may include Tenax™ TA porous polymer resin material available from Buchem B.V.

The preconcentrator is coupled to the GC column valve manifold 302 at the first end 306 of the preconcentrator 300. The GC column valve manifold 302 may be coupled to the gas valve manifold 210 of the sparger assembly 104 and may direct the carrier gas stream that has passed through the water sample and that includes the VOCs through the preconcentrator 300. The GC column valve manifold 302 may also be coupled to the GC column assembly 108 and may also direct carrier gas stream passed through the preconcentrator 300 (e.g., during the desorption step 1006) to the GC column assembly 108. Operation of the GC column valve manifold 302 may be provided by controlling one or more actuators, solenoids, pumps associated therewith (exemplified at 320, 322 in FIG. 7). Control may be carried out by the control module 112.

The preconcentrator 300 is coupled to the preconcentrator vent valve manifold 304 at the second end 308 of the preconcentrator 300. The preconcentrator vent valve manifold 304 may be coupled to one of the outputs 146 of the housing assembly 128 and may be configured to direct the carrier gas stream flow that has passed through the preconcentrator 300 out of the housing assembly 128 through the output 146. The preconcentrator vent valve manifold 304 may also be coupled to one of the inputs 146 of the housing assembly and may also be configured to direct a carrier gas stream from the gas supply 148 to the preconcentrator 300 in the opposite direction of the flow of gas during the collection step 1004. Operation of the preconcentrator vent valve manifold 304 may be provided by controlling one or more actuators, solenoids, pumps associated therewith (exemplified at 324 in FIG. 7). Control may be carried out by the control module 112.

In some embodiments, the preconcentrator assembly 106 includes a preconcentrator heater 312. The preconcentrator heater 312 may be wrapped around at least a portion of the preconcentrator 300 and may heat the preconcentrator 300 during the desorption step 1006 to encourage the sorbent material to release the adsorbed compounds into the carrier gas stream, which may in-turn be directed by the GC column valve manifold 302 to the GC column assembly 108.

In some embodiments, the preconcentrator assembly 106 includes a preconcentrator cooling fan 314. When activated, the preconcentrator cooling fan 314 may draw air circulating within the enclosure 136 of the housing assembly 128 and may direct it across the preconcentrator heater 312 to provide heat transfer from the preconcentrator heater 312 to the air stream for rapid cooling. The heat transferred to the air may then be exhausted and dispersed back into the circulating air stream within the enclosure 136 of the housing assembly 128.

Accordingly, with reference to the sparger assembly 104 and the and the preconcentrator assembly 106 shown in the figures, the carrier gas having the entrained VOCs may be passed from the gas valve manifold 210 and through the preconcentrator assembly 106. In the preconcentrator assembly, the carrier gas may pass through the GC column valve manifold 302, the preconcentrator 300, the vent valve manifold 304, and the output 146. When the carrier gas passes through the preconcentrator 300, the VOCs entrained in the stream may be adsorbed by the sorbent bed disposed in the preconcentrator. The sparging and associated passing of the carrier gas through the preconcentrator may be conducted for any suitable amount of time. In some embodiments, the duration of the sparging process may range from about 2 minutes to about 30 minutes.

With continued reference to FIG. 3, at step 1006, the preconcentrator 300 is heated via the preconcentrator heater 312 and the VOCs adsorbed by the sorbent bed 310 disposed in the preconcentrator 300 may be desorbed. The preconcentrator 300 may be heated by the preconcentrator heater 312 to any suitable temperature. At the elevated temperature, the VOCs may desorb from the sorbent material and may be entrained by a carrier gas passing therethrough. In an example, the preconcentrator 300 may be heated via the preconcentrator heater 312 to a temperature in the range of about 150° C. to about 350° C. The duration of the desorption process may range from about 1 second to about 5 minutes. Carrier gas may be input through the housing 128 via an input 144, may pass through the preconcentrator vent valve manifold 304, and may enter the preconcentrator 300 in a direction opposite the flow of the carrier gas in the collection step 1004. The carrier gas passing through the preconcentrator 300 and that includes the desorbed VOCs may pass through the GC column valve manifold 302 and may be provided to the GC column assembly 108.

Figure 8:
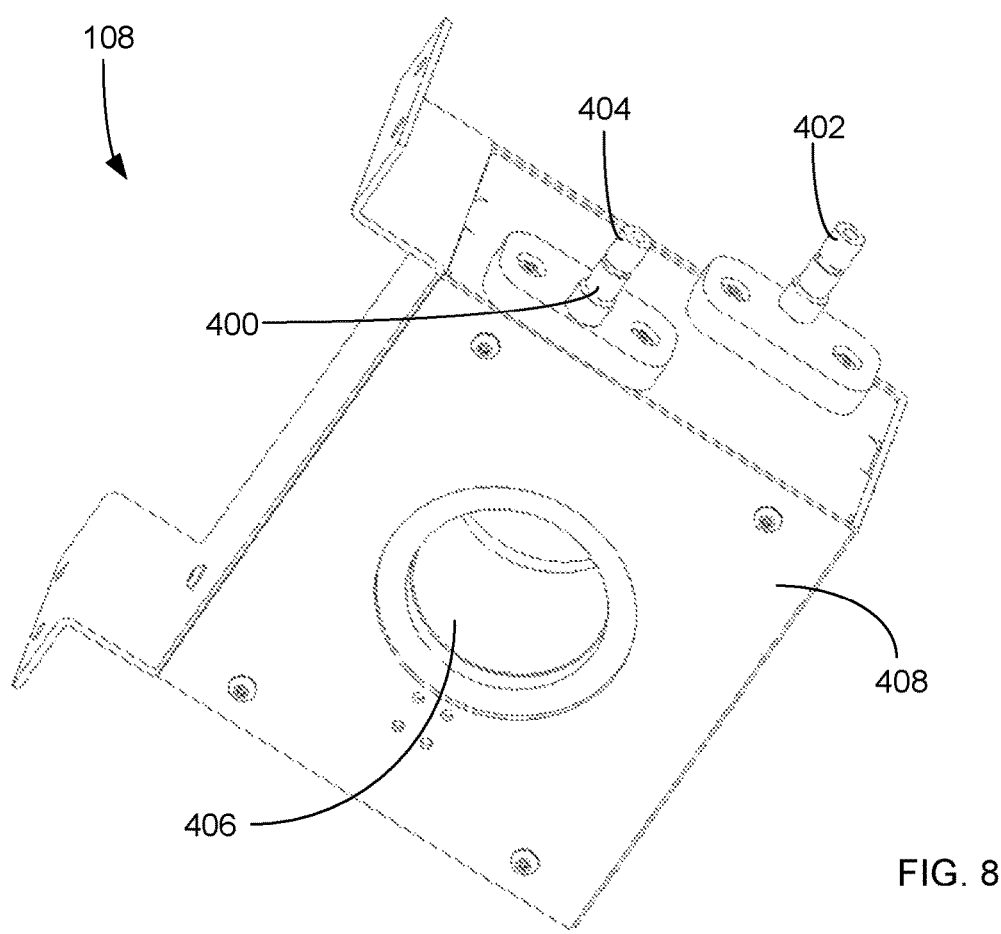
FIG. 8 is schematic perspective illustration of an exemplary GC column assembly in accordance with the present disclosure.

At step 1008, the carrier gas including the VOCs desorbed from the preconcentrator 300 is passed through the GC column assembly 108. Referring now to FIG. 8, the GC column assembly 108 includes a GC column 400. The GC column 400 is coupled at a first end 402 to the GC column valve manifold 302 of the preconcentrator assembly 106. The GC column 400 is coupled at a second end 404 to the SAW detector assembly 110. The GC column 400 may provide compound separation prior to delivery of the VOCs to the SAW detector assembly 110 for compound quantification. The GC column 400 partially retains the VOCs with different affinities as they pass through the column, resulting in different retention times for each compound and thereby spreading out the time each compound is delivered to the detector.

The GC column 400 may be a tubular member having a small diameter and a suitable length. The GC column 400 may be internally coated with specific adsorbent materials that can be selected for the type of compounds to be detected. In some embodiments, the length of the GC column may be about 6 meters to about 60 meters. In other embodiments, the length of the GC column may be about 6 meters to about 15 meters. In some embodiments, the inner diameter of the GC column may be about 0.25 mm to about 1.0 mm. In other embodiments, the coating thickness of the coating in the GC column may be about 0.10 µm to about 8 µm.

In some embodiments, the GC column assembly 108 includes a column heater 406. The GC column 400 may be in close contact with (e.g., wrapped around) the column heater 406. In some embodiments, the column heater 406 may be a membrane heater.

In some embodiments, the GC column assembly 108 includes a housing 408 that encloses the GC column 400 and column heater 406. The housing 408 may be mounted to the backplate 124.

Accordingly, with reference to the figures, the carrier gas including the desorbed VOCs may pass through the GC column 400, and due to the different retention time in the GC column (due to the different affinities as they pass through the column), the VOCs are delivered to the SAW detector at different retention times. In an example, the GC column 400 may be heated via the column heater 406 to a temperature in the range of about 35° C. to about 300° C. In another example, the GC column 400 may be heated via the column heater 406 to a temperature in the range of about 35° C. to about 200° C. Passing the carrier gas including the desorbed VOCs through the GC column 400 may be carried out simultaneously with the desorption step, and therefore the duration of this step may be the same as the duration of the desorption process (e.g., 1 second to about 5 minutes).

With continued reference to FIG. 3, at step 1010, the VOCs passed through the GC column and delivered to the SAW detector assembly 110 and are detected and analyzed. The SAW detector assembly 110 includes a SAW detector. The SAW detector may include a piezoelectric element having a surface coated on its sensing surface with a material selected to adsorb and interact with the VOCs to be detected. In some embodiments, the SAW detector includes a nanoporous carbon surface coating. The SAW detector detects the presence of VOCs by adsorbing and then desorbing the compounds as they cross the surface of the coating. Interaction of the compound with the material coating of the sensing element alters one or more properties of a surface acoustic wave, and the electrodes on the piezoelectric element detect the altered wave, producing an electrical signal. The electric signal can be analyzed to determine the presence/concentration of the various VOCs.

Figure 9:
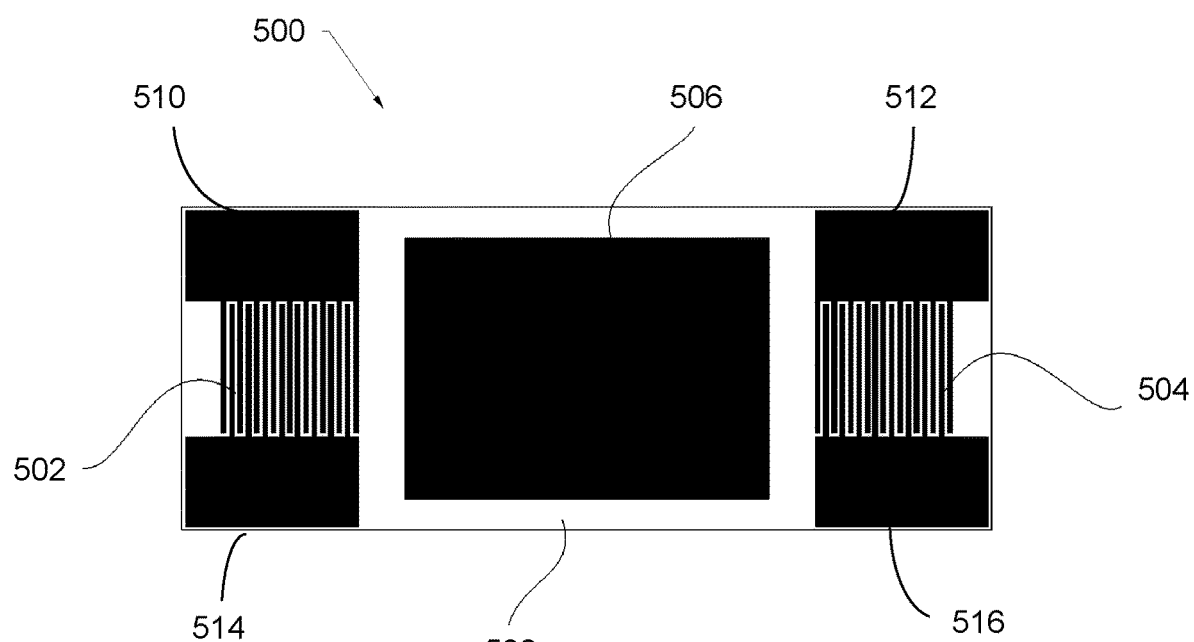
FIG. 9 is a schematic illustration of an exemplary SAW detector in accordance with the present disclosure.

FIG. 9 is a depiction of an exemplary 100 MHz SAW detector 500 including input and output transducers (e.g. IDT fingers) 502 and 504 and having a nanoporous carbon coating 506 applied to the sensing surface 508 of the SAW detector 500 using pulsed-laser deposition. The SAW detector 500 also includes Pogo pin contact points 510, 512, 514, 516. The nanoporous carbon coating 506 adsorbs and desorbs the organic compounds. The frequency of the SAW device changes as a function of the change in adsorbed mass of these organic compounds. This change of frequency is converted into a voltage signal according to mass adsorption and desorption on the SAW device.

As described above, the housing assembly 128 may isolate the components disposed therein from the external environment. For example, the housing assembly 128 may reduce the effect that the ambient temperature of the environment has on the analysis system 100 (e.g., by reducing the amount of heat transferred between the enclosure 136 of the housing assembly 128 and the ambient environment that is external to the housing assembly 128). The housing assembly 128 may also isolate the components disposed therein from other conditions such as dust, insects, moisture, and humidity.

Isolation of the components within the housing may create thermal management issues. For example, heat produced by components of the analysis system 100 such as the electronics (e.g., the one or more interface boards 120, 122), the heated sparger assembly 104, the heated preconcentrator assembly 106, and the heated GC column assembly 108 can shift the temperature within the housing assembly 128 or may create hot/cold spots within the housing assembly 128. The shifted temperature and/or the hold/cold spots may differ from the temperature at which the analysis system is calibrated. The analysis system 100 may be controlled (e.g., by the control module) to repeatedly test water samples at a given interval (e.g., once per hour, once every 5 hours, or at another suitable interval), and this repeated testing may frequently add heat to the interior (enclosure 136) of the housing assembly 128. In addition, even though the thermal conductivity between the enclosure 136 of the housing assembly 128 and the ambient environment that is external to the housing assembly 128 may be low, this thermal conductivity may still have the effect of lowering or raising the temperature within the housing assembly 128 to above or below the temperature at which the analysis system is calibrated. These conditions will negatively affect such things as the amount of VOC compounds extracted from the water sample and compound retention times in the GC column, thereby affecting the accuracy and reliability of the analysis system.

Conventional laboratory GC instruments are typically vented with fans used to draw in cooler room air and exhaust heated air to maintain acceptable and stable internal temperatures. However, in a non-laboratory environment, using ambient air for cooling will expose the instrument components to elements such as room humidity, dust, and corrosive vapors, thereby defeating the purpose of the sealed enclosure. Additionally, the potentially wide range of ambient temperature can, during venting, expose the analysis system 100 to either very cold air, creating cold spots within the analyzer and causing condensation of moisture and/or analytes; or very hot air, the air being potentially too hot to permit adequate analyzer cooling. Either condition, hot or cold, can also cause measurement error should instrument temperature vary significantly from calibration temperature.

The analysis system 100 in accordance with the present disclosure includes one or more thermal management features that may allow the conditions of the testing environment within the housing to be as close to ideal as possible (e.g., as close to the calibration temperature as possible). This control may be realized without utilizing external air venting. The one or more thermal management features (e.g., the air circulation assembly 151 (FIGS. 13 and 14) and/or the heat exchanger assembly 158) may be referred to as a thermal control assembly.

As described above, in some embodiments, the components of the analysis system may be configured to work more effectively within the isolated system. For example, the thermal insulation 142 on the interior walls and cover of the housing assembly may reduce the heating and cooling load resulting from ambient air temperature differences with the enclosure temperature. In another example, the Faraday cage 126 that may enclose the electronics to control EMC emissions is perforated to permit more efficient convective heat transfer of the waste heat generated by the electronics. This may help to maintain a lower electronics board temperature which improves the uniformity of the enclosure temperature. In another example, the length and mass of the CG column may be minimized, which may reduce the heat input required to raise the column temperature to elute the VOCs. In another example, the electric solenoid valves included in the analysis system 100 may be operated initially at full voltage to assure full actuation and immediately thereafter at reduced voltage required to maintain the valves in the energized position. This may reduce the temperature rise in the solenoid coils. In another example, the SAW detector 500 may only require low DC voltage and very little power to operate. Unlike other GC detectors, such as an FID, ECD or Mass Spectrum, there is comparatively little waste heat generated.

Figure 5:
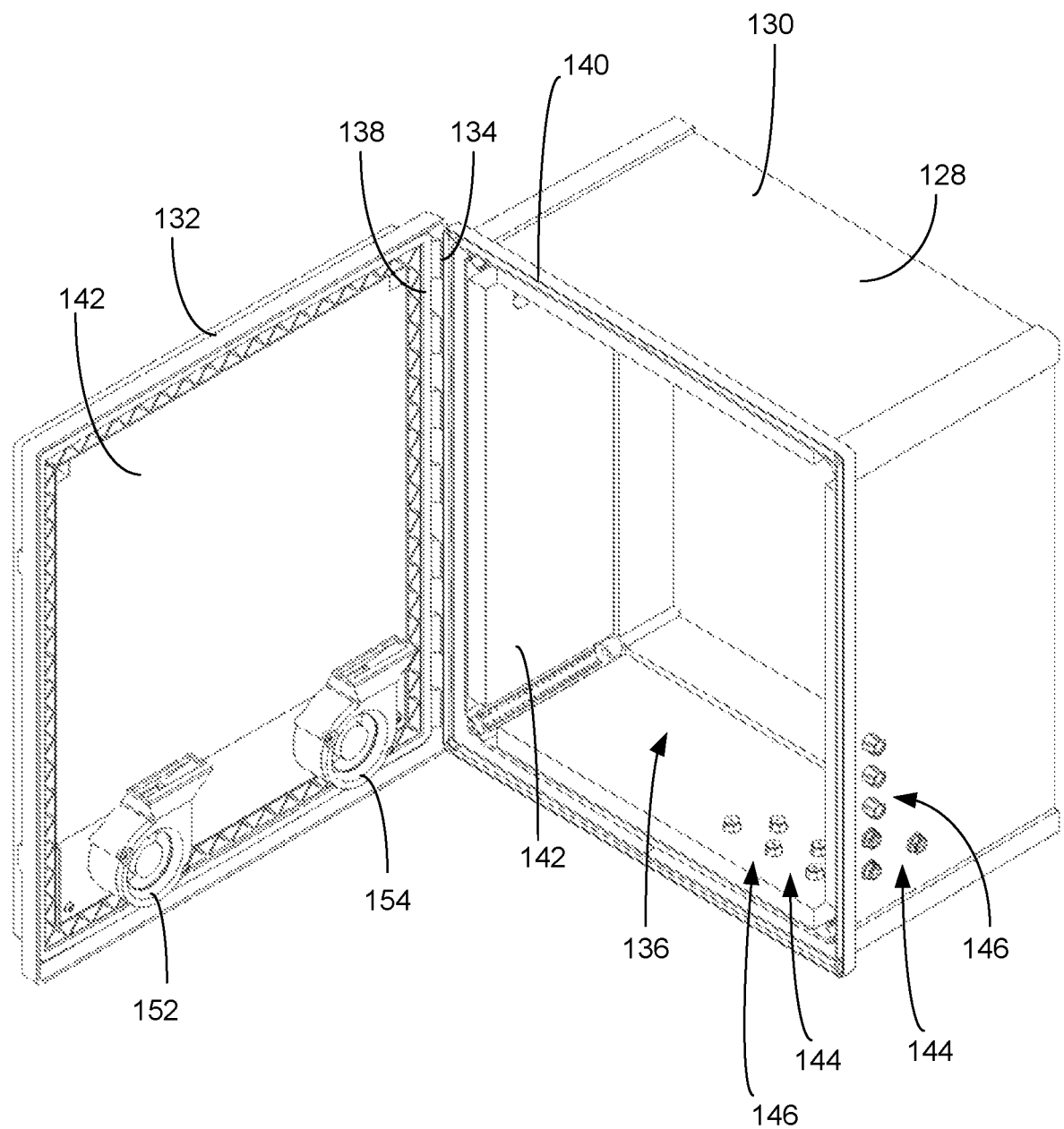
FIG. 5 is a schematic perspective illustration of components of an exemplary analysis system in accordance with the present disclosure.

In addition to the above, in some embodiments, the analysis system 100 includes an air circulation assembly 151 (FIGS. 13 and 14) within the housing 128. As shown in FIGS. 1 and 5, air circulating fans 152 and 154 are mounted to the housing cover 132. As further shown in FIG. 10, an air circulating fan 156 may be mounted on the back surface of the backplate 124. These air circulating fans 152, 154, 156 may assist in circulating air within the housing assembly 128 to eliminate temperature stratification and to help maintain a more even and constant temperature within the enclosure 136 of the housing assembly 128. In the example shown, the fans may be respectively arranged to output air in opposite directions (e.g., fans 152, 154 and fan 156) and thereby establish the air circulation within the housing assembly.

Figure 10:
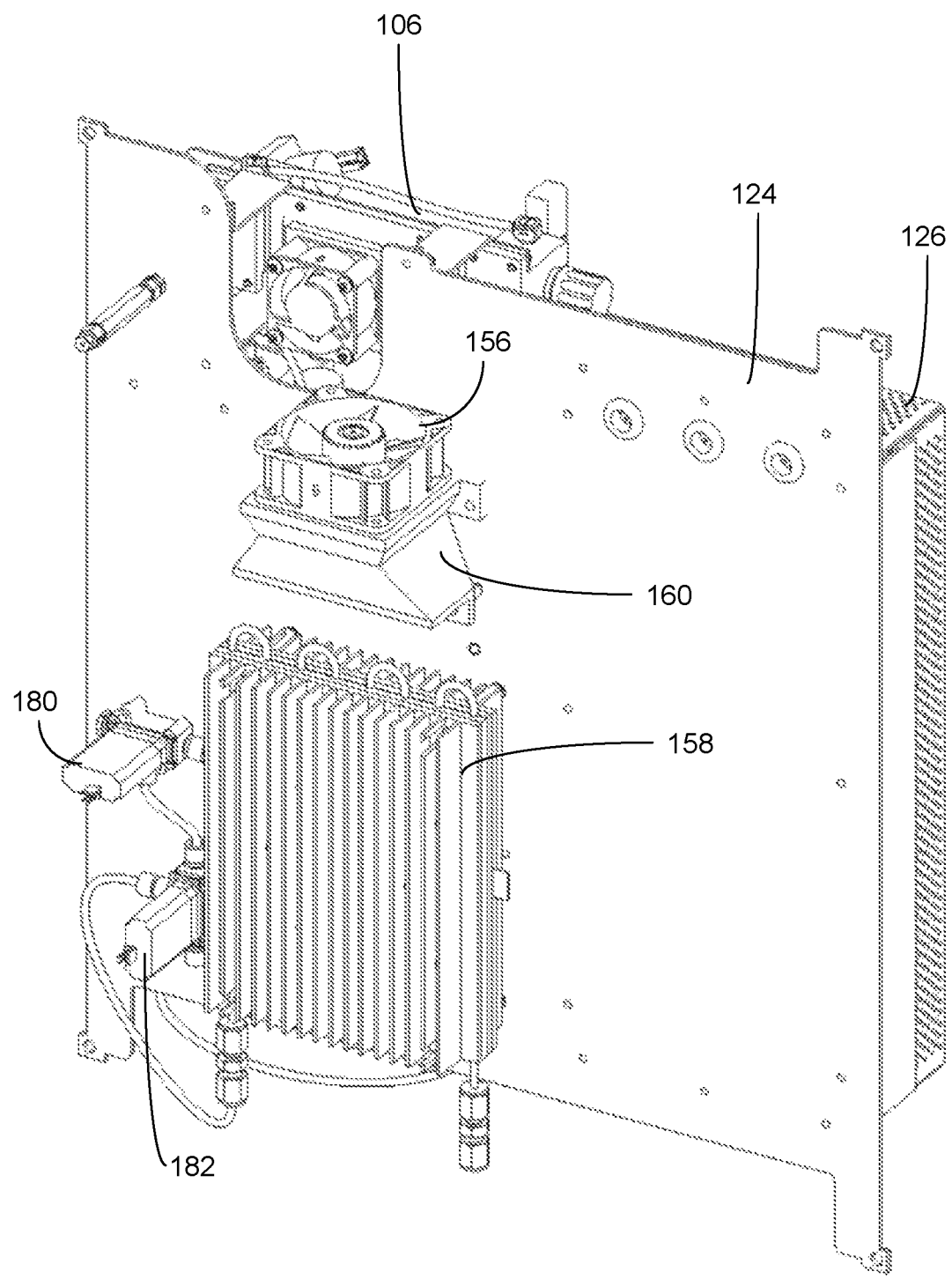
FIG. 10 is schematic perspective illustration of components of an exemplary analysis system in accordance with the present disclosure.

FIG. 10 further shows that a heat exchanger assembly 158 may be mounted to the back surface of the backplate 124 (e.g., to the surface of the backplate opposite the surface on which the VOC detection assembly 102 is mounted). The heat exchanger assembly 158 may assist in cooling or heating the circulating air, depending on the temperature of the circulating air inside the housing assembly 128 relative to a programmed set temperature.

Figure 11:
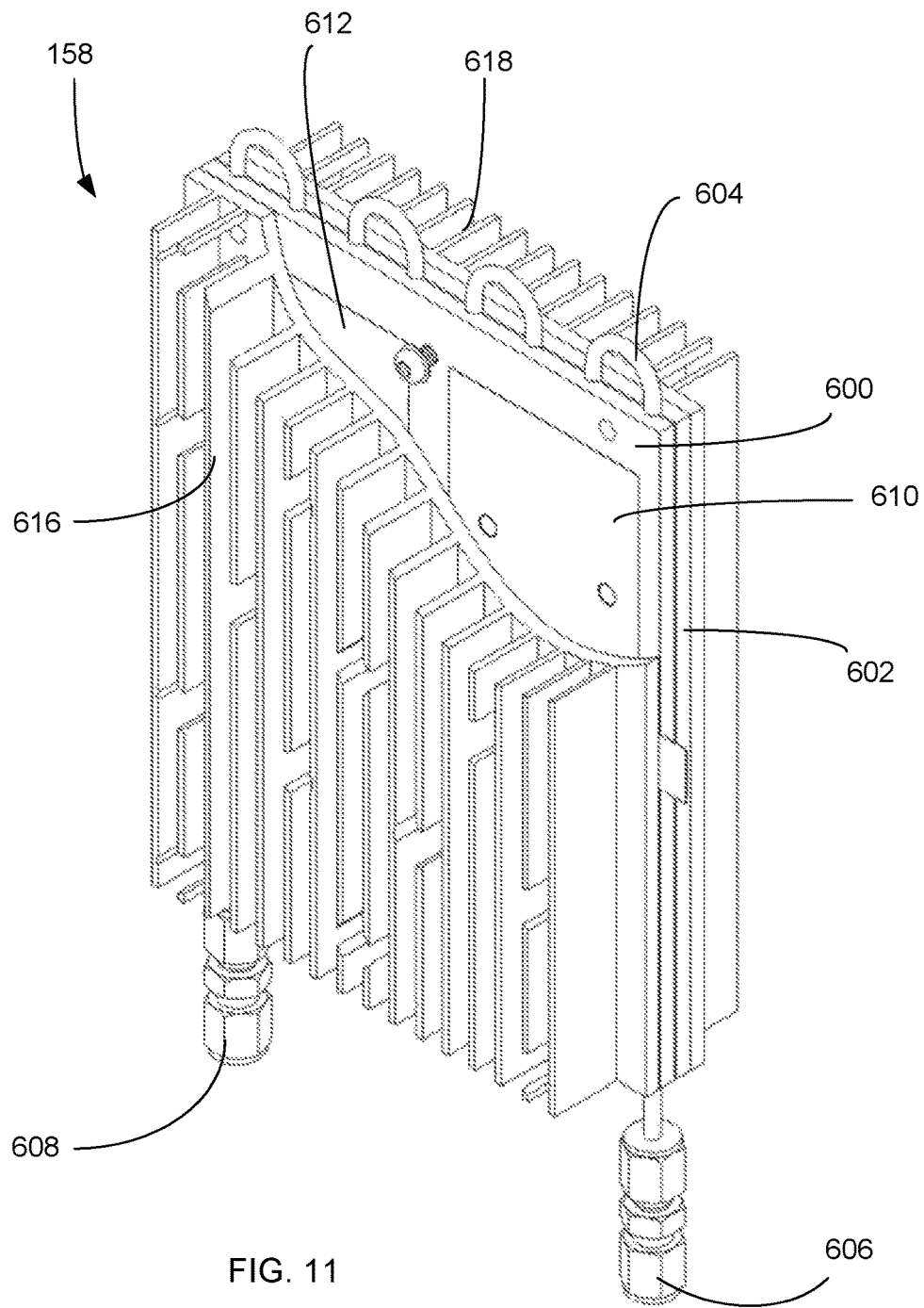
FIG. 11 is a schematic perspective illustration of an exemplary heat exchange assembly in accordance with the present disclosure.

With additional reference to FIG. 11, the heat exchanger assembly 158 may include a pair of core plates 600, 602. The core plates 600, 602 may be made from a material having a high thermal conductivity, such as a metallic material (e.g., copper). In some embodiments, one or both of the core plates 600, 602 may be grooved, and within this groove a cooling tube 604 may pass. The cooling tube 604 may be made from a material having a high thermal conductivity, such as a metallic material (e.g., copper). As an example, one of the core plates may include a groove on its face that is sufficient for the cooling tube 604 to be disposed therein when the faces of the core plates are brought together. As another example, each of the core plates 600, 602 includes a groove formed on its face, and the respective grooves may collectively form a path when the faces of the core plates are brought together in which the cooling tube 604 may be disposed. As shown in the exemplary embodiment, the cooling tube 604 may be arranged in a serpentine configuration between the core plates 600, 602. A first portion 606 of the cooling tube 604 extends from the core plates 600, 602, which may serve as an inlet connection. This inlet connection may be coupled to an inlet 144 of the housing assembly 128. A second portion 608 of the cooling tube 604 extends from the core plates 600, 602, which may serve as an outlet connection. This outlet connection may be coupled to an outlet 146 of the housing assembly 128. A fluid (e.g., a liquid) may pass through the cooling tube 604 and may effectuate removal of heat from the heat sink assembly. In some embodiments, the cooling fluid may be a refrigerant. In other embodiments, the cooling fluid may be water. As an example, the water may be water that is drawn from the water source (water supply 150) being tested. The water may be input to the housing assembly through the first portion of the cooling tube extending from the input of the housing assembly, may pass through the portion of the cooling tube disposed between the core plates, and may be through the second portion of the cooling tube extending from the core plates to the output of the housing assembly. The use of water as the cooling fluid may allow for lower power demands as compared with the use of a refrigerant.

Use of the water from the water supply 150 for the cooling fluid may provide several advantages. For example, the water will be available at the remote location where the water is to be sampled and analyzed; and the water will generally be available as a pressurized supply of water. When the pressure from the water source and drain is large enough, the water can flow through the heat exchanger unaided by a pump (whether external or internal to the housing assembly 128. Otherwise, when the pressure from the water is inadequate, a water pump can be used to supply the required pressure. The water flow rate can also be controlled by using a pressure regulator to set water pressure at the inlet of the heat exchanger to a predetermined level. Moreover, the water temperature may be cooler than the ambient air temperature at the remote location (or at least cool enough for sufficient cooling of the enclosure 136 of the housing assembly 128) since it is common for water to be transported in pipes buried in the ground. But in some embodiments, the water may be cooled prior to entering the housing assembly 128 using equipment such as any commercially available water chiller (not shown). This cooling may be employed to augment the water cooling potential.

Figure 12:
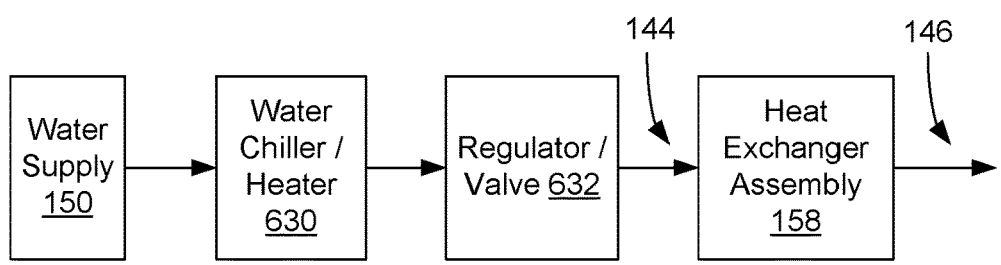
FIG. 12 is a schematic illustration of a water supply connected to components of an exemplary analysis system in accordance with the present disclosure.

Exemplary use of the water from the water supply 150 for the cooling fluid is schematically illustrated in FIG. 12. In the exemplary embodiment shown, the water supply 150 is coupled to a water chiller/heater 630, which as described above, may provide temperature control of the water. The water chiller/heater 630 is in-turn coupled to a regulator/valve 632, which as described above, may provide flow/pressure control of the water. From the regulator/valve 632, the water may be input through the input 144 of the housing 128 and may be coupled to the heat exchanger assembly 158. Upon passing through the heat exchanger assembly 158, the water may exit the analysis system 100 via the output 146.

Operation of the heat exchanger assembly 158 may be provided by controlling one or more actuators, solenoids, pumps associated therewith (exemplified at 180 and 182 of FIG. 10). Control may be carried out by the control module 112. In some embodiments, the control module may also be configured to control operation of the chiller/heater 630 and the regulator/valve 632.

With continued reference to FIG. 11, the heat exchanger assembly 158 may include one or more heating elements 610, 612. In one example, the one or more heating element 610, 612 may be embodied as flexible membrane heater. This membrane type heater may be disposed between one or more layers of the heat exchanger assembly 158. As shown, the one or more heating elements 610, 612 may be provided on the outer face of at least one of the core plates 600, 602. The one or more heating elements 600, 602 may add heat from the heat exchanger assembly 158 to the circulating air in the enclosure 136 of the housing.

The heat exchanger assembly 158 may include finned heat exchanger plates 616, 618. In some embodiments, the finned heat exchanger plates are mechanically mounted to the outer faces of the core plates 600, 602 to maintain close thermal contact therebetween. As shown, in some embodiments, the heating elements 610, 612 may be disposed between the core plate and the finned heat exchanger plate. The finned heat exchanger plates 616, 618 may be made from a material having a high thermal conductivity, such as a metallic material (e.g., copper). The fins of the finned heat exchanger plates 616, 618 may increase the surface area of the heat exchanger assembly 158, which may help to maximize heat transfer between the heat exchanger assembly 158 and the circulating air in the enclosure 136 of the housing assembly 128.

The combination of the metal core plates 600, 602, the finned heat exchanger plates 616, 618, the one or more heating elements 610, 612, and the cooling tube 604 may create a large thermal mass. A large thermal mass combined with a large heat transfer surface area may assist in temperature control and stability because it provides for increased thermal inertia which then permits an increased amount of heat transferred between the circulating air inside of the housing assembly 128 and the heat exchanger assembly 158.

As shown in FIG. 10, an air focusing duct 160 may be disposed between the air circulating fan 156 and the heat exchanger assembly 158. The air focusing duct 160 may focus the air output by the air circulating fan 156 in the direction of and over the surface (e.g., over finned heat exchanger plates 616, 618 of the heat exchanger assembly 158. This may increase heat transfer between the heat exchanger assembly 158 and the circulating air.

The thermal system may maintain control of the interior (enclosure 136) temperature of the housing assembly 128 in accordance with input from one or more thermocouples 190 (FIGS. 13 and 14) located in the circulating air stream generated by the circulating fans in the enclosure. One exemplary thermocouple 190 is shown in the figures at an exemplary location, but in other embodiments, the thermocouple 190 may be located at a different location in the circulating air stream. Additionally, in other embodiments, more than one thermocouple 190 may be located throughout the circulating air stream. The one or more thermocouples 190 may be used to compare the temperature of the circulating air to a set temperature (or temperature range). If the temperature of the circulating air falls below the set temperature (or temperature range), the heat exchanger assembly 158 may be controlled to increase the temperature of the circulating air. If the temperature of the circulating air rises above the set temperature (or temperature range), the heat exchanger assembly 158 may be controlled to decrease the temperature of the circulating air. In some embodiments, the set temperature (or temperature range) of the interior (enclosure 136) of the housing 128 may be about 20° C. to about 40° C. In other embodiments, the set temperature (or temperature range) of the interior (enclosure 136) of the housing 128 may be about 25° C. to about 35° C.

Figure 13:
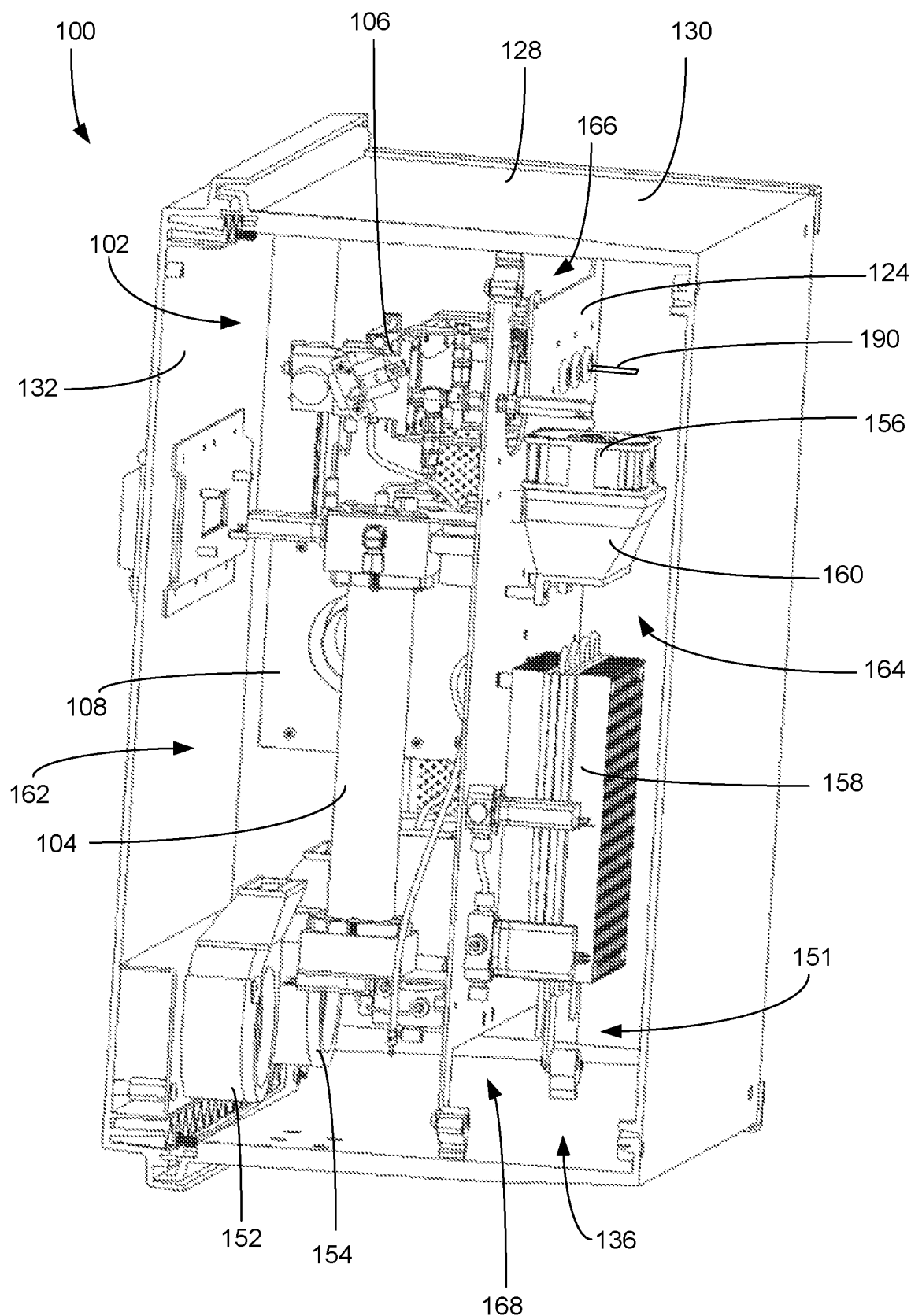
FIG. 13 is schematic perspective illustration of components of an exemplary analysis system in accordance with the present disclosure.
Figure 14:
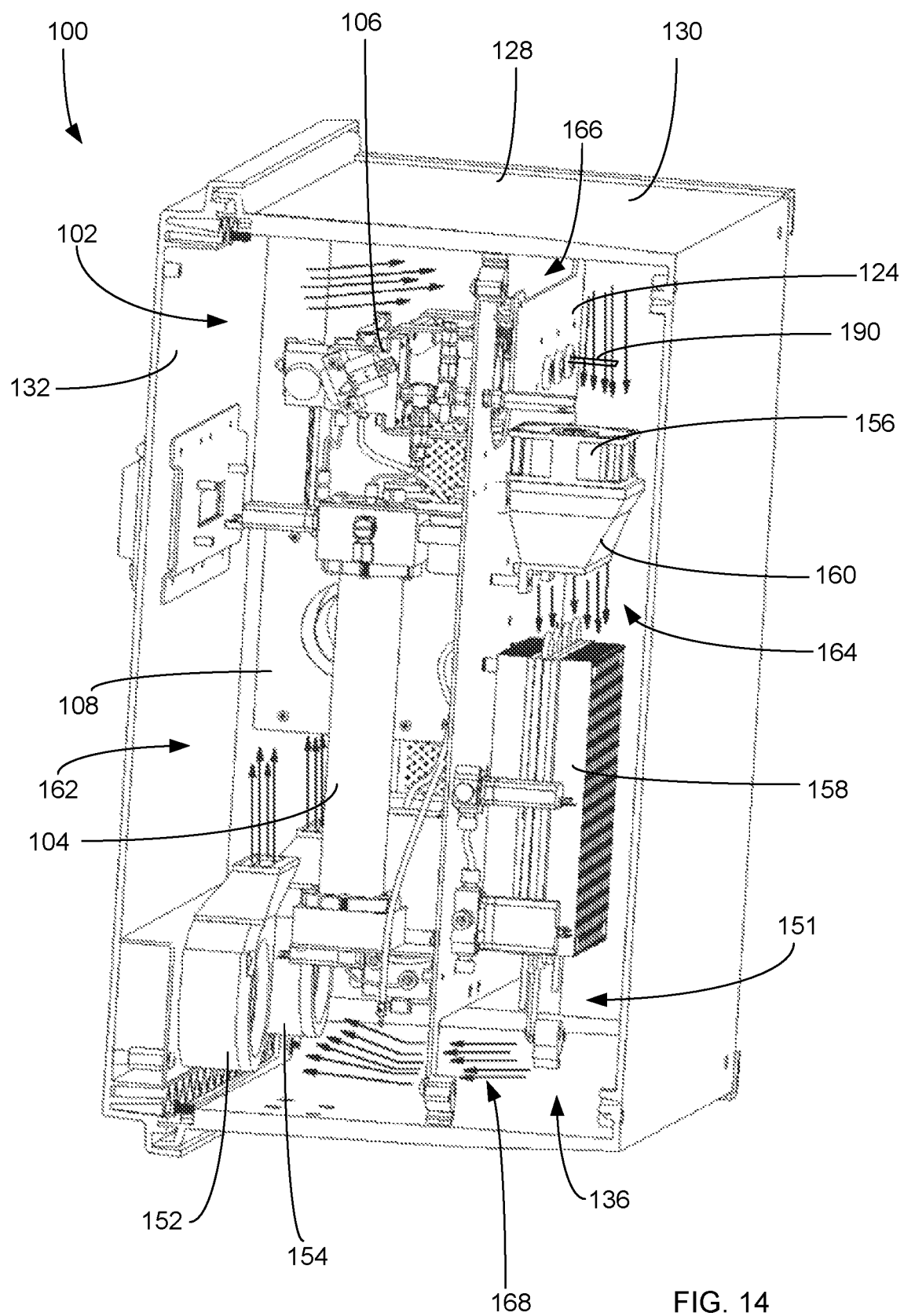
FIG. 14 is schematic perspective illustration of components of an exemplary analysis system in accordance with the present disclosure.

Now referring to FIGS. 13 and 14, circulation of the air in the enclosure 136 of the housing assembly 128, and temperature control using the heat exchanger assembly 158 is described in more detail. FIGS. 13 and 14 show similar schematic views of the analysis system 100, but FIG. 14 includes arrows to schematically show the flow vectors of the air within the housing assembly 128.

As shown, the backplate to which components of the analysis system 100 are mounted may be positioned in the enclosure 136 of the housing assembly 128 in a central or offset location to provide an air gap 162, 164 on each side of the backplate 124. Cutouts 166, 168 are respectively provided at the top and bottom locations of the backplate, which each provide an air passage between and fluidly connect the air gaps 166, 168 located on the opposite sides of the backplate 124. The air gaps 166, 168 permit, via the circulating air fans 152, 154, 156, the establishment of a continuous flow of circulating air around the VOC detection assembly 102.

The flow direction of the circulating air, driven by the circulating air fans 152, 154, 156, is illustrated by the flow vector arrows in FIG. 14. In the embodiment shown, the flow may be upward in the air gap 162 proximate the housing cover 132, due to the location of the waste heat generated by the electronics, the sparger assembly 104, the GC column assembly 108, and the preconcentrator assembly 106. The inlet air to the circulating air fans 152, 154 may be drawn through the cutout 168 at the bottom of the backplate 124 from the air gap 164 proximate the opposite side of the backplate 124 after the air has been directed past the heat exchanger assembly 158 by the circulating air fan 156 and the focusing duct 160. The air output by the circulating air fans 152, 154, as well as the heated air at the front side of the backplate may be directed upward to the top of the enclosure and, may pass through the cutout 166 at the top of the backplate 124, and may be pushed/pulled downward toward the circulating air fan 156, focusing duct 160, and heat exchanger assembly 158.

While the VOC detection assembly 102, may run periodically (e.g., depending on the set intervals between the testing processes), the circulating air fans 152, 154, 156 may run continuously, enveloping the components of the VOC detection assembly 102 in a constant flow of temperature controlled air. Dependent upon the requirement detected by the control system (e.g., via the one or more thermocouples 190 located in the enclosure 136 of the housing 128), heat may be either added to or taken from the circulating air.

In one example, when the one or more thermocouples 190 located in the enclosure 136 of the housing 128 senses that the temperature is below the set temperature (or temperature range), then the control module 112 may provide electrical current to the two heating elements 610, 612 of the heat exchanger assembly 158. This may raise the temperature of the heat exchanger assembly 158 which may in turn raise the temperature of the circulating air by transferring heat thereto as the air is passed over the surface of the heat exchanger assembly 158. The precision of temperature control can be controlled by controlling the amount of electrical current delivered to the heating elements 610, 612 (e.g., as a function of the differential between the temperature of the circulating air and the set temperature or temperature range). Upon application of the current to the heating elements 610, 612, when the one or more thermocouples 190 senses the temperature above a given set point, the control module 112 may stop providing electrical current to the two heating elements 610, 612. The given set point may be the calibration temperature or may be a temperature close to (e.g., within 1° C. to 5° C.) the calibration temperature.

In another example, when the one or more thermocouples 190 located in the enclosure 136 of the housing 128 senses that the temperature is above the set temperature (or temperature range), then the control module 112 may control the heat exchanger assembly 158 to start the flow of cooling liquid (e.g., water from the water source) through the cooling tube 604. This may lower the temperature of the heat exchanger assembly 158 which may in turn lower the temperature of the circulating air by transferring heat therefrom as the air is passed over the surface of the heat exchanger assembly 158. The heat transferred from the circulating air may be transferred to the cooling liquid flowing through the cooling tube 604, which may be disposed outside of the housing assembly 128 when the cooling liquid exits through the outlet 146 of the housing assembly. When the one or more thermocouples 190 senses that the temperature is below a given set point, then the electronics control module 112 stop the flow of cooling water through the cooling tube 604 embedded in the heat exchanger assembly 158. The given set point may be the calibration temperature or may be a temperature close to (e.g., within 1° C. to 5° C.) the calibration temperature. To prevent the growth of undesirable organics, a purge air valve may be connected to the carrier gas supply can be momentarily enabled to allow carrier gas to flow through the cooling tube 604 to purge out water remaining in the tube.

As described above, the cooling capacity available from the water passed through the cooling tube 604 may be dependent upon the water temperature and its flow rate. Accordingly, in some embodiments, the cooling capacity of the water can be controlled by controlling one or both of the inlet water temperature and flow rate. As an example, as discussed above with reference to FIG. 12, the flow rate of the water can be controlled by controlling the pressure of the water using an adjustable pressure regulator or a variable control valve 632. In another example, the temperature of the water can be controlled by employing a chiller 630 to lower the cooling water temperature prior to inputting the water into the cooling tube 604.

The features of the analysis system 100 in accordance with the present disclosure, namely the thermal management features, may improve the accuracy and/or reliability of the VOC analysis performed by the system. For example, the interior (enclosure 136) temperature of the housing assembly may be maintained at a constant programmable level throughout a wide range of ambient (outside of the enclosure) temperature. The interior temperature of the housing assembly may also be maintained at a constant programmable level despite the VOC detection assembly 102 periodically performing analysis of water samples. This may assure that a consistent amount of THM or other VOC compounds are extracted during sparging, resulting in reliable, accurate and consistent measurement regardless of the ambient environment temperature. This may also eliminate the need for complex and less reliable calibration adjustment factors used for estimating measurements when the water sample temperature varies from the calibration temperature.

In another example, by maintaining a stable temperature inside the housing assembly, moisture in the sparge gas stream may be prevented from condensing into water droplets inside the gas pathways or the sorbent bed of the preconcentrator. This may assure that moisture in the sparge gas stream can be exhausted to atmosphere after passing through the preconcentrator, preventing excessive moisture from being directed into the GC column assembly 108 and SAW detector assembly 110 or causing condensation problems in valves or the trap sorbent bed 310 of the preconcentrator 300. In another example, by maintaining a stable temperature inside the housing assembly, VOCs in the sparge gas stream may be prevented from condensing inside the gas pathways before reaching the sorbent bed of the trap. This may help to ensure consistently accurate and reliable measurement results. In another example, by maintaining a stable temperature inside the housing assembly, the compound retention times in the GC column may be prevented from shifting relative to the times established during instrument calibration.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An analysis system, comprising:
    a housing assembly defining an enclosure;
    a volatile organic compound detection assembly enclosed in the enclosure of the housing assembly, the volatile organic compound detection assembly configured to detect a volatile organic compound in a liquid sample, wherein the volatile organic compound detection assembly is embodied as a purge and trap gas chromatography system, comprising:
        a sparger assembly enclosed in the enclosure of the housing assembly and configured to retain the liquid sample and sparge volatile organic compounds from the liquid sample;
        a preconcentrator assembly enclosed in the enclosure of the housing assembly and configured to adsorb the volatile organic compounds passing therethrough and desorb the adsorbed volatile organic compounds for analysis;
        a gas chromatograph column assembly enclosed in the enclosure of the housing assembly and configured to separate the volatile organic compounds passed therethrough; and
        a surface acoustic wave detector enclosed in the enclosure of the housing assembly and configured to detect a mass of organic compounds separated by a gas chromatograph column; and
    a thermal control assembly enclosed in the enclosure of the housing assembly, the thermal control assembly comprising:
        a fan arranged to circulate air enclosed within the housing assembly, the volatile organic compound detection assembly arranged in a path of the circulating air; and
        a heat exchanger assembly arranged to control a temperature of the circulating air.

2. The analysis system of claim 1, wherein the heat exchanger assembly comprises:
    a plurality of core plates; and
    a cooling tube having its length partially disposed between the core plates, a first portion of the cooling tube extending from the core plates and coupled a second input of the housing assembly configured to input cooling liquid from a liquid source external to the housing, a second portion of the cooling tube extending from the core plates and coupled to an output configured to output from the housing assembly the cooling liquid passing through the cooling tube.

3. The analysis system of claim 2, wherein the heat exchanger assembly further comprises at least one heating element.

4. The analysis system of claim 2, further comprising a backplate to which at least a portion of the volatile organic compound detection assembly is mounted, the backplate enclosed in the housing and arranged in a central or offset location to provide an air gap on each side of the backplate, the heat exchanger mounted to an opposite side of the backplate to which the at least a portion of the volatile organic compound detection assembly is mounted.

5. The analysis system of claim 4, wherein the backplate comprises cutouts at top and bottom locations of the backplate, each cutout providing an air passage between the air gaps.

6. The analysis system of claim 1, wherein the fan is proximate the heat exchanger assembly and is arranged to output at least a portion of the circulating air in the direction of and over the surface of the heat exchanger assembly.

7. The analysis system of claim 6, wherein the thermal control assembly further comprises an air focusing duct disposed between the fan and the heat exchanger assembly, the air focusing duct configured to focus the air output by the fan in the direction of and over the surface of the heat exchanger assembly.

8. The analysis system of claim 1, wherein the housing does not include a fan or vent connecting the enclosure of the housing assembly to an ambient environment in which the analysis system is located.

9. The analysis system of claim 1, further comprising a backplate to which at least a portion of the volatile organic compound detection assembly is mounted, the backplate enclosed in the housing and arranged in a central or offset location to provide an air gap on each side of the backplate, wherein the backplate comprises cutouts at top and bottom locations of the backplate providing an air passage between and fluidly connecting the air gaps.

10. A method of detecting a volatile organic compound in a liquid sample, comprising:
    conducting a volatile organic compound detection process by controlling a volatile organic compound detection assembly, the volatile organic compound detection assembly enclosed within a housing assembly, the housing assembly comprising an input for inputting the liquid sample from a liquid source external to the housing assembly, wherein the volatile organic compound detection process comprises:
- sparging the liquid sample with a sparging assembly enclosed within the housing assembly;
- collecting the volatile organic compound with a preconcentrator assembly enclosed within the housing assembly;
- desorbing the volatile organic compound from the preconcentrator assembly enclosed within the housing assembly;
- separating the volatile organic compound as desorbed from the preconcentrator assembly with a gas chromatograph column assembly enclosed within the housing assembly; and
- detecting the mass of the volatile organic compound separated by the gas chromatograph column assembly with a surface acoustic wave detector enclosed within the housing assembly; and
- controlling a thermal control assembly enclosed in the housing assembly, the thermal control assembly comprising a fan and a heat exchanger assembly, the control of the thermal control assembly comprising:
  - operating the fan within the housing assembly to circulate air enclosed within the housing, the volatile organic compound detection assembly in a path of the circulating air; and
  - controlling a temperature of the circulating air with the heat exchanger assembly.

11. The method of claim 10, wherein the control of the thermal control assembly comprises:
- inputting cooling liquid from a liquid source external to the housing assembly through a cooling tube that has a first portion extending from an input of the housing assembly to a plurality of core plates of the heat exchanger assembly, and
- outputting the cooling liquid through a second portion of the cooling tube extending from the core plates to an output of the housing assembly.

12. The method of claim 10, wherein the control of the thermal control assembly further comprises controlling a heating element in physical contact with one of the core plates.

13. The method of claim 10, wherein the control of the thermal control assembly comprises operating the fan proximate the heat exchanger assembly to direct at least a portion of the circulating air in the direction of and over the surface of the heat exchanger assembly.

14. The method of claim 10, wherein the air is circulated around a backplate enclosed in the housing assembly to which at least a portion of the volatile organic compound detection assembly is mounted, the backplate arranged in a central or offset location to provide an air gap on each side of the backplate and comprising cutouts at top and bottom locations of the backplate to fluidly connect the air gaps.

15. An analysis system, comprising:
- a housing main body;
- a cover removably attached to the main body and enclosing an interior of the housing assembly from an ambient environment in which the analysis system is located;
- a volatile organic compound detection assembly enclosed in the enclosure of the housing assembly, the volatile organic compound detection assembly configured to detect a volatile organic compound in a liquid sample;
- a backplate enclosed in the housing main body and arranged in a central or offset location therein to provide an air gap on each side of the backplate, the backplate comprising cutouts at top and bottom locations of the backplate, each cutout providing an air passage between the air gaps;
- a fan enclosed in the housing main body and arranged to circulate the air enclosed within the housing assembly; and
- a heat exchanger assembly enclosed in the housing main body and configured to control a temperature of the circulating air,
wherein at least a portion of the volatile organic compound detection assembly is mounted to the backplate and the heat exchanger assembly is mounted to an opposite side of the backplate to which the at least a portion of the volatile organic compound detection assembly is mounted.

16. The analysis system of claim 15, wherein the heat exchanger assembly comprises:
- a plurality of core plates; and
- a cooling tube having its length partially enclosed between the core plates, a first portion of the cooling tube extending from the core plates and coupled an input of the housing assembly configured to input cooling liquid from a liquid source external to the housing, a second portion of the cooling tube extending from the core plates and coupled to an output of the housing assembly configured to output from the housing assembly the cooling liquid passing through the cooling tube.

17. The analysis system of claim 16, wherein the heat exchanger assembly further comprises at least one heating element.

* * * * *